US009453032B2

(12) United States Patent
Sutton et al.

(10) Patent No.: US 9,453,032 B2
(45) Date of Patent: Sep. 27, 2016

(54) BROAD SPECTRUM BETA-LACTAMASE INHIBITORS

(71) Applicant: GLADIUS PHARMACEUTICALS CORPORATION, Montreal (CA)

(72) Inventors: Larry Sutton, Atchison, KS (US); Sophia Yu, Atchison, KS (US)

(73) Assignee: GLADIUS PHARMACEUTICALS CORPORATION, Montreal, Quebec (CA)

( * ) Notice: Subject to any disclaimer, the term of this patent is extended or adjusted under 35 U.S.C. 154(b) by 0 days.

(21) Appl. No.: 14/491,806

(22) Filed: Sep. 19, 2014

(65) Prior Publication Data
US 2015/0011524 A1    Jan. 8, 2015

Related U.S. Application Data

(63) Continuation of application No. 12/248,760, filed on Oct. 9, 2008, now Pat. No. 8,883,772.

(60) Provisional application No. 60/997,898, filed on Oct. 9, 2007, provisional application No. 60/997,941, filed on Oct. 9, 2007.

(51) Int. Cl.
*C07D 501/22* (2006.01)
*C07D 501/24* (2006.01)
*C07D 501/60* (2006.01)
*A01N 43/90* (2006.01)
*A61K 31/00* (2006.01)

(52) U.S. Cl.
CPC ............. *C07D 501/60* (2013.01); *A01N 43/90* (2013.01); *C07D 501/22* (2013.01); *C07D 501/24* (2013.01)

(58) Field of Classification Search
CPC   C07D 501/60; C07D 501/24; C07D 501/22; A01N 43/90
See application file for complete search history.

(56) References Cited

U.S. PATENT DOCUMENTS

| | | | |
|---|---|---|---|
| 3,830,700 A | 8/1974 | O'Callaghan et al. |
| 3,971,778 A | 7/1976 | Cook et al. |
| 3,983,113 A | 9/1976 | Beeby |
| 4,065,620 A | 12/1977 | Webber |
| 4,094,978 A | 6/1978 | Beeby |
| 4,103,084 A | 7/1978 | Bradshaw et al. |
| 4,152,432 A | 5/1979 | Heymes et al. |
| 4,255,423 A | 3/1981 | Beattie et al. |
| 4,307,116 A | 12/1981 | Farge et al. |
| 4,307,233 A | 12/1981 | Farge et al. |
| 4,342,758 A | 8/1982 | Firestone |
| 4,346,218 A | 8/1982 | Tsuji et al. |
| 4,365,062 A | 12/1982 | Farge et al. |
| 4,380,512 A | 4/1983 | Gottstein |
| 4,385,181 A | 5/1983 | Farge et al. |
| 4,388,326 A | 6/1983 | Firestone |
| 4,500,457 A | 2/1985 | Gosteli et al. |
| 4,520,022 A | 5/1985 | Hoshi et al. |
| 4,558,071 A | 12/1985 | Firestone |
| 4,616,084 A | 10/1986 | Häbich et al. |
| 4,639,448 A | 1/1987 | Takaya et al. |
| 4,654,359 A | 3/1987 | Firestone |
| 4,760,067 A | 7/1988 | Firestone |
| 4,839,350 A | 6/1989 | Atsumi et al. |
| 4,870,168 A | 9/1989 | Baker et al. |
| 4,952,690 A | 8/1990 | Gosteli et al. |
| 4,988,686 A | 1/1991 | Atsumi et al. |
| 5,061,702 A | 10/1991 | Atsumi et al. |
| 5,073,551 A | 12/1991 | Kobori et al. |
| 5,151,417 A | 9/1992 | Sasho et al. |
| 5,171,854 A | 12/1992 | Schmidt et al. |
| 5,336,768 A | 8/1994 | Albrecht et al. |
| 5,373,001 A | 12/1994 | Aszodi et al. |
| 5,541,175 A | 7/1996 | Yeo et al. |
| 5,656,754 A | 8/1997 | Torii et al. |
| 5,936,083 A | 8/1999 | Aszodi et al. |
| 6,133,441 A | 10/2000 | Wagner |
| 6,248,881 B1 | 6/2001 | Wieser et al. |
| 6,417,351 B1 | 7/2002 | Kameyama |
| 6,576,761 B1 | 6/2003 | Tanaka et al. |
| 6,897,304 B2 | 5/2005 | Kawashima et al. |
| 2005/0124580 A1 | 6/2005 | Freire et al. |

(Continued)

FOREIGN PATENT DOCUMENTS

| | | |
|---|---|---|
| CA | 1340154 | 12/1998 |
| CA | 1340424 | 3/1999 |

(Continued)

OTHER PUBLICATIONS

Examination Report corresponding to European Patent Application No. 08837969.8, dated Nov. 5, 2014.
Notice of Reasons for Rejection corresponding to Japanese Patent Application No. P2010-529054, dated Aug. 19, 2014—with English translation.
Ambler, R.P. (1980) "The Structures of β-Lactamases," *Philos. Trans. R. Sci. Lond. B. Biol. Sci.* 289:321-323.
Aszodi J. et al. (1993) "Vinylogous vs. Arylogous Isocephems" Bioorganic Med. Chem. Letts 3(11):2231-2236 (Pergamon Press).
Bird et al. (1992) "Pharmacokinetics of catechol cephalosporins. The effect of incorporating substituents into the catechol moiety on pharmacokinetics in a marmoset model," *Journal of Medicinal Chemistry.* 35:2643-2651.

(Continued)

*Primary Examiner* — Samantha Shterengarts
*Assistant Examiner* — Matt Mauro
(74) *Attorney, Agent, or Firm* — Lathrop & Gage LLP

(57) ABSTRACT

Broad spectrum beta-lactamase inhibitors. Certain inhibitors also exhibit potent antibiotic activity in addition to beta-lactamase inhibition. Compounds of the invention are designed such that on cleavage of the beta-lactam ring reactive moieties are generated which can inactivate beta-lactamase. Also provided are methods of making beta-lactamase inhibitors and beta-lactam antibiotics exhibiting such inhibition. Additionally provided are pharmaceutical compositions for treatment or prevention of bacterial infections and methods of treatment of such infections.

25 Claims, 13 Drawing Sheets

(56) References Cited

U.S. PATENT DOCUMENTS

| | | | |
|---|---|---|---|
| 2008/0200447 A1 | 8/2008 | Koppel | |
| 2010/0261700 A1 | 10/2010 | Sutton et al. | |

FOREIGN PATENT DOCUMENTS

| | | | |
|---|---|---|---|
| EP | 0025857 | | 4/1981 |
| EP | 0292808 | | 11/1988 |
| EP | 0408034 | | 1/1991 |
| EP | 0623622 | | 11/1994 |
| EP | 0691343 | | 1/1996 |
| EP | 0357089 | | 3/1996 |
| JP | S55-154980 | | 12/1980 |
| JP | S61-178991 | | 8/1986 |
| JP | S63-307885 | | 12/1988 |
| JP | H03-005486 | | 1/1991 |
| JP | WO 93/16043 | * | 8/1993 |
| JP | H08-283273 | | 10/1996 |
| WO | WO 2009/049086 | | 4/2009 |
| WO | WO 2010/118361 | | 10/2010 |

OTHER PUBLICATIONS

Boyde et al. (1979) "Electronic Structures of Cephalosporins and Penicillins. 9. Departure of a Leaving Group in Cephalosporins," *J. Med. Chem.* 22(7):778-784.

Buynak et al. (2004) "The Discovery and Development of Modified Penicillin- and Cephalosporin-Derived a-Lactamase Inhibitors," *Current Medicinal Chemistry.* 11:1951-1964.

Buynak, J.D. (2006) "Understanding the Longevity of the β-Lactam Antibiotics and of Antibiotic/β-Lactamase Inhibitor Combinations," *Biochem. Pharmacol.* 71:930-940.

Drawz et al. (Jan. 2010) "Three Decades of β-Lactamase Inhibitors," *Clin. Microbiol. Rev.* 23(1):160-201.

Extended European Search Report corresponding to European Patent Application No. 08837969.8, dated Jun. 25, 2013.

Fina et al. (Jan. 26, 1973) "The Alpha Effect. A Review," *Int. J. Chem. Kinetics* 5(1):1-26.

Fisher et al. (Web Release Feb. 9, 2005) "Bacterial Resistance to β-Lactam Antibiotics: Compelling Opportunism, Compelling Opportunity," *Chem. Rev.* 105:395-424.

Goossens et al. (Sep. 5, 1998) "Community Acquired Infections and Bacterial Resistance," *British Med. J.* 317:654-657.

Grekov et al. (1978) "The Alpha-Effect in the Chemistry of Organic Compounds," *Russian Chem. Rev.* 47(7):631-648.

Hickey et al. (May 2007) "Hydrates and Solid-State Reactivity: A Survey of β-Lactam Antibodies," *J. Pharmaceutical Sci.* 96(5):1090-1099.

Hooton et al. (Mar. 15, 2001) "Antimicrobial Resistance: A Plan of Action for Community Practice," *Am. Fam. Physician* 63(6):1087-1096.

Hun Yeong Koh et al. (19960 "Synthesis and 1-4, 7, Structure-Activity Relationships of Cephalosporins having a Catechol Moiety," Korean Journal of Medicinal Chemistry. 6:333-338.

International Search Report and Written Opinion, Corresponding to International Application No. PCT/US08/79410, Mailed Dec. 12, 2008.

International Search Report and Written Opinion, Corresponding to International Application No. PCT/US10/30590, Mailed Jun. 28, 2010.

Jamieson et al. (Aug. 2003) "In Vitro Activities of Novel Oxapenems, Alone and in Combination with Ceftazidime, Against Gram-Positive and Gram-Negative Organisms," *Antimicrob. Agents Chemother.* 47(8):2615-2618.

Jones et al. (1999) "Epidemiologic Trends in Nosocomial and Community-Acquired Infections Due to Antibiotic-Resistant Gram-Positive Bacteria: The Role of Streptogramins and Other Newer Compounds," *Diagn. Microbiol. Infect. Dis.* 33:101-112.

Jones, R.N. (Feb. 2001) "Resistance Patterns Among Nosocomial Pathogens—Trends Over the Past Few Years," *Chest* 119(2):397S-404S (supp).

Lee et al. (Web Release Dec. 2, 2004) "A Practical Synthesis of Nitrocefin," *J. Org. Chem.* 70(1):367-369.

Naito T. et al. (1987) "Synthesis and Structure-Activity Relationship of a New Oral Cephalosporin, BMY-28100 and Related Compounds" Journal Antibiotics (Tokoyo) vol. XL (7):991-1005 (Japan Antibiotics research Association).

Notice of Reasons for Rejection corresponding to Japanese Patent Application No. P2010-529054, dated Jul. 23, 2013.

Sandanayaka et al. (2002) "Resistance to β-Lactam Antibiotics: Structure and Mechanism Based Design of β-Lactamase Inhibitors," *Curr. Med. Chem.* 9:1145-1165.

Sutton et al. (1995) "Development, Characterization, and Initial Evaluations of S1—A New Chromogenic Cephalosporin for β-Lactamase Detection," *Diag. Microbiol. Infect. Dis.* 21:1-8.

Tanaka et al. (2001) "Reductive Cross-Coupling of 3-Substituted Delta$^3$-Cephems with Alkenyl Halides in an Al/PbBr2/NiBr2(bpy) Triplemetal Redox System. Synthesis of 3-Alkenyl-Delta$^3$-cephems," *Journal of Organic Chemistry.* 66:570-577.

Wilke et al. (2005) "β-Lactam Antibiotic Resistance: A Current Structural Perspective," *Curr. Opni. Microbiol.* 8:525-533.

Yamazaki et al. (2000) "Novel Cephalosporins 2. Synthesis of 3-Heterocyclic-fused Thiopyranylthiovinyl Cephalosporins and Antibacterial Activity against Methicillin-resistant *Staphylococcus aureus* and Vancomycin-resistant *Enterococcus faecalis*," *Journal of Antibiotics.* 53:546-550.

* cited by examiner

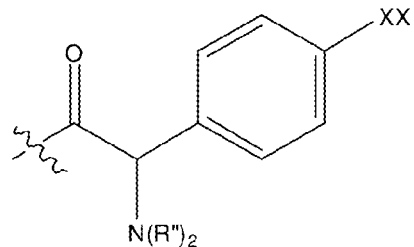
A15
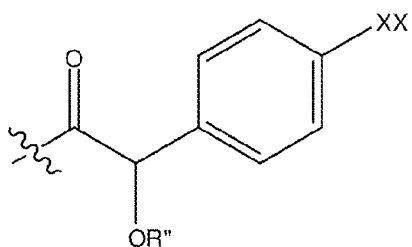
A16
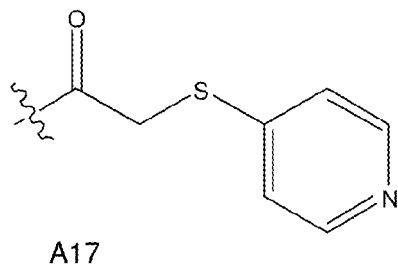
A17
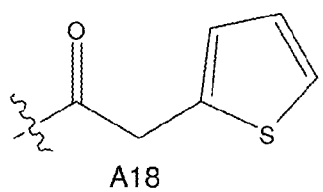
A18
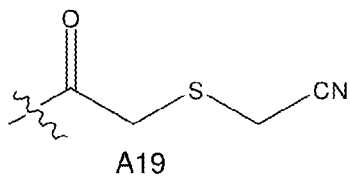
A19
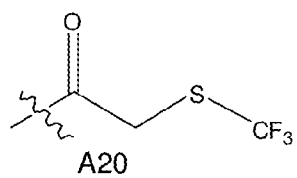
A20
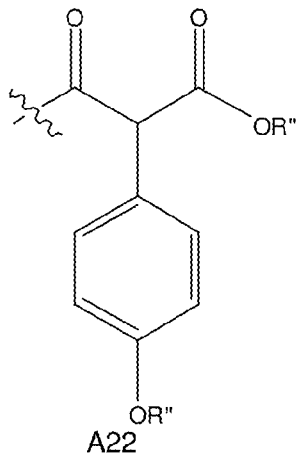
A22
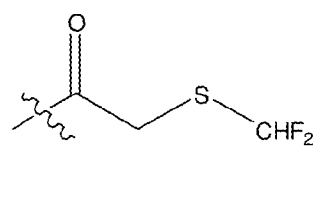
A21
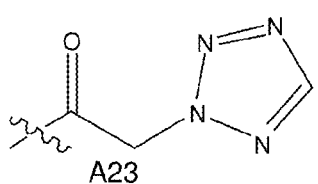
A23
FIG. 3-1

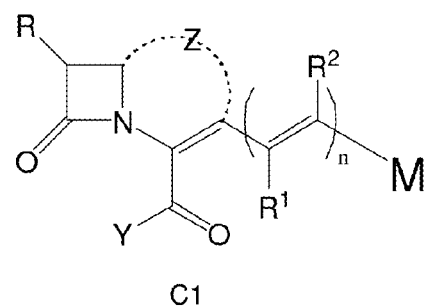
C1
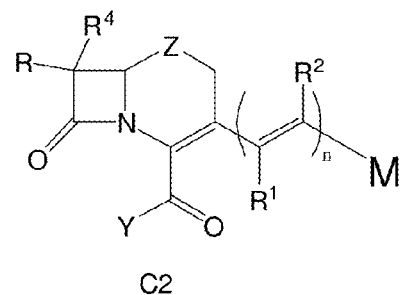
C2
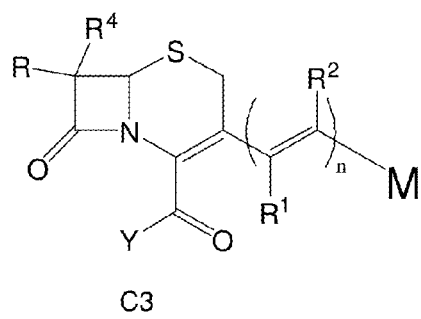
C3
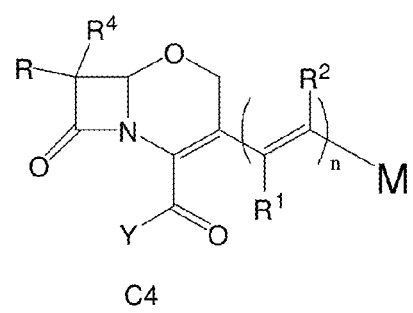
C4
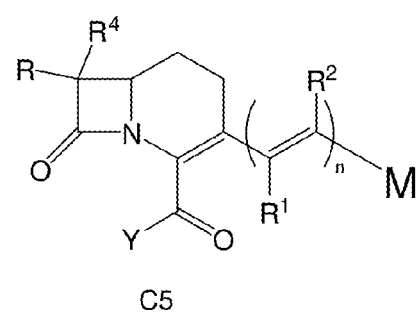
C5
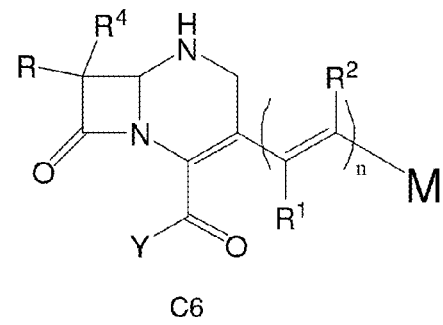
C6
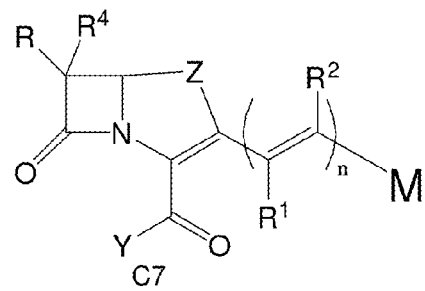
C7
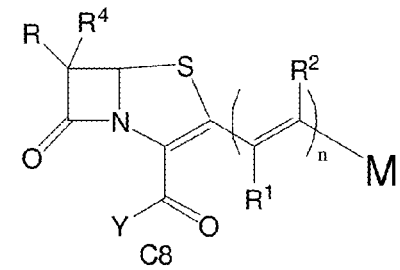
C8
FIG. 4-1

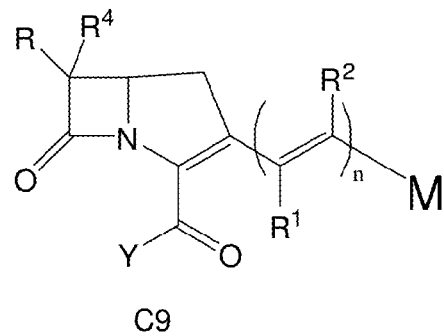
C9
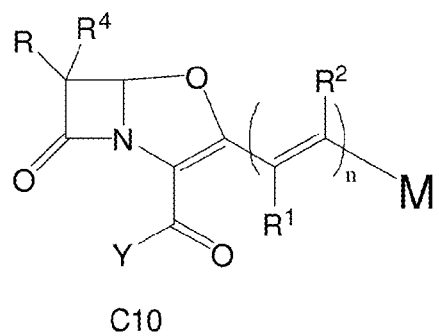
C10
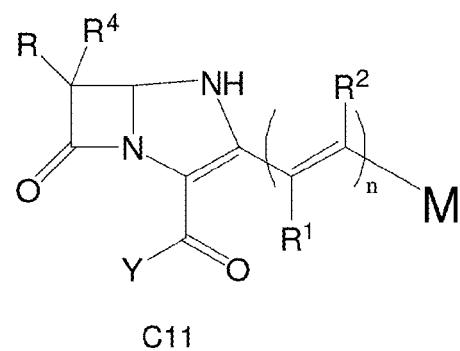
C11
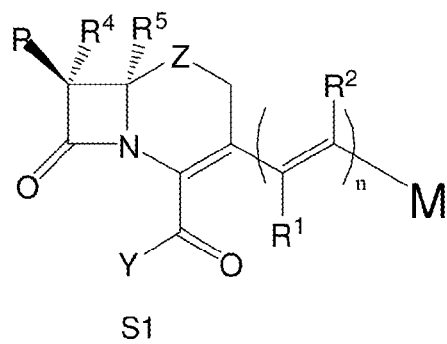
S1
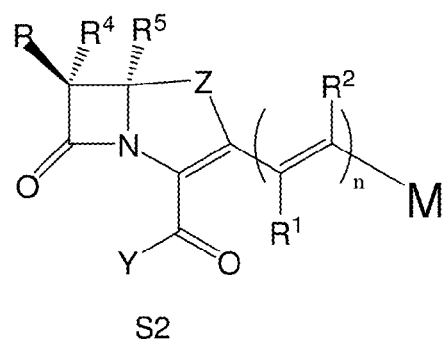
S2
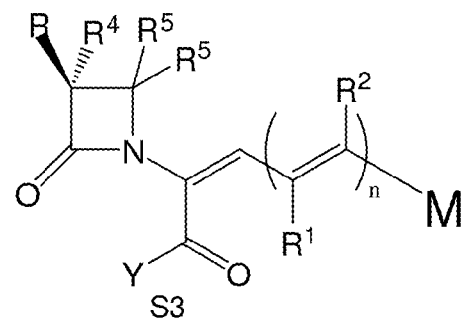
S3
FIG. 4-2

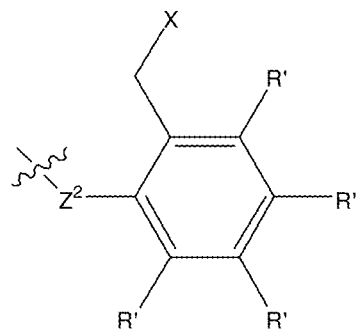
BZ1
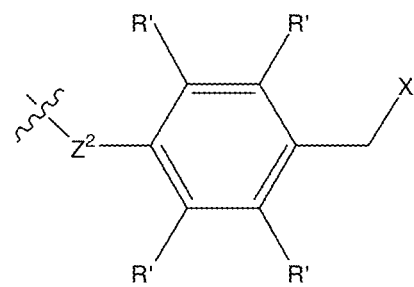
BZ2
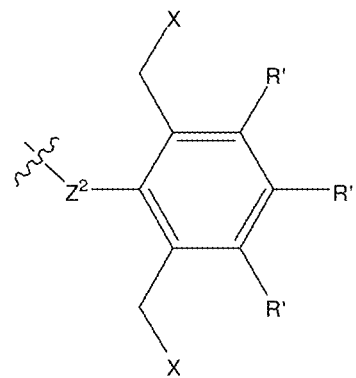
BZ3
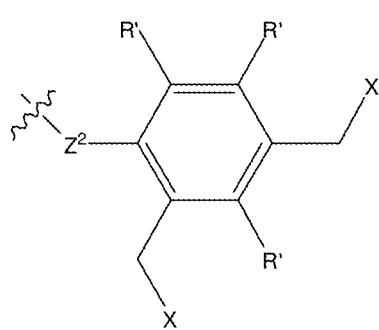
BZ4
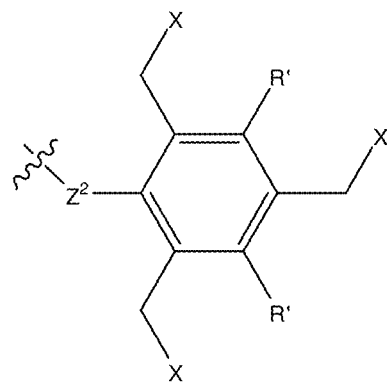
BZ5
Fig. 5-3

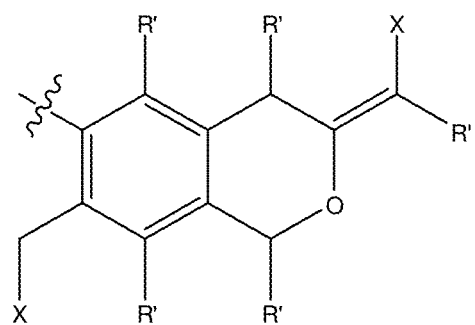 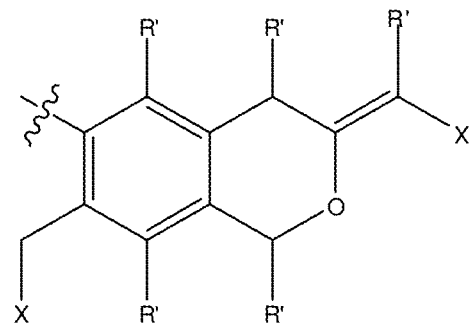
F5          F6
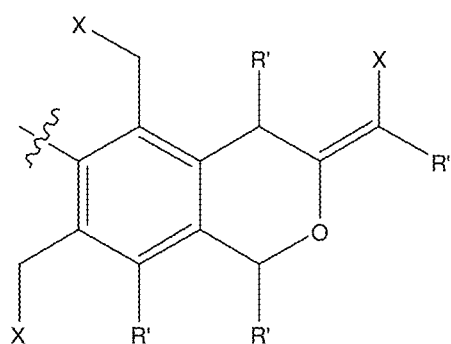 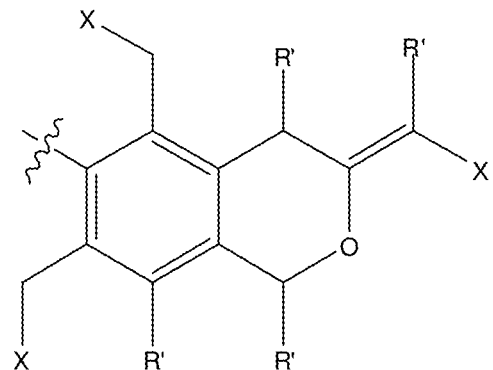
F7          F8
FIG. 5-6

BROAD SPECTRUM BETA-LACTAMASE INHIBITORS

CROSS-REFERENCE TO RELATED APPLICATIONS

This application is a continuation of copending U.S. application Ser. No. 12/248,760, filed Oct. 9, 2008, which claims the benefit of and priority to U.S. Provisional Application Nos. 60/997,898 and 60/997,941, both filed Oct. 9, 2007. Each of these applications is incorporated by reference herein in its entirety.

BACKGROUND OF THE INVENTION

The present invention relates to beta-lactamase inhibitor compounds, their production and use.

The invention and use of antibiotics to cure infectious diseases caused by bacteria is one of the milestones of modem medical and scientific technology. The beta-lactam class of antibiotics has been and continues to be one of the most important. Antibiotic resistance has become a major problem worldwide. One of the most important resistance mechanisms to beta-lactam antibiotics is the bacterial production of beta-lactamases, enzymes that inactivate beta-lactam antibiotics by catalyzing the hydrolysis of the lactam ring rendering the antibiotics ineffective towards binding of their target, penicillin binding protein.

Previous attempts to circumvent inactivation by beta-lactamases have been to alter beta-lactam compounds by functionalizing them with various organic groups conferring resistance to beta-lactam hydrolysis while maintaining antimicrobial potency. However, evolution of beta-lactamases has kept pace and there is now a beta-lactamase that is able to inactivate every known clinically available beta-lactam antibiotic; over 500 beta-lactamases have been documented.

Broadly defined by mechanism there are two fundamental classes of beta-lactamases, serine hydrolases and metallo-hydrolases. The enzymes can be further classified by sub-dividing them into groups according to their spectrum of activity towards beta-lactam compounds. The serine hydrolases are sub-classified into Bush Class A which are the penicillinases. Class C enzymes refer to the cephalosporinases. While Class D enzymes are the broad spectrum or extended spectrum beta-lactamases (ESBL). Bush Class B beta-lactamases refer to the metallo-enzymes that require one or two Zn2+ ions for activity and likewise show a broad spectrum of activity towards beta-lactam antibiotics. Another strategy has been to develop and use inhibitors of beta-lactamases. Three compounds are currently in clinical use, clavulanic acid, sulbactam and tazobactam.

These compounds irreversibly inhibit Class A penicillinases. Drawbacks of the known inhibitors are that they possess little intrinsic antimicrobial activity and therefore must be used in combination with beta-lactam antibiotics. The second shortcoming is that they are not clinically effective at inhibiting Classes B, C, and D enzymes which are increasingly important.

Thus, there is a significant need in the art for potent beta-lactam antibiotic compositions which demonstrate the additional functionality of potent beta-lactamase inhibition while maintaining antimicrobial potency.

SUMMARY OF THE INVENTION

The invention relates to compounds which are beta-lactamase inhibitors and particularly relates to beta-lactam antibiotics that also exhibit inhibition of beta-lactamase. The invention is further directed to methods of making such compounds and methods of using such compounds for inhibition of microbial growth.

In an embodiment, the invention provides compounds of formula I:

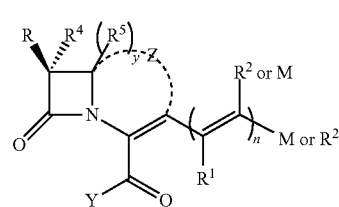

and pharmacologically acceptable salts thereof wherein:

R is a pharmaceutically acceptable functional group including, an acylamino group, and pharmaceutically acceptable salts thereof;

$R^1$, $R^2$, $R^3$, $R^4$ and $R^5$ are selected from hydrogen or a wide range of organic groups;

n is an integer ranging from 1-5 and is preferably 1;

—Z— is a linker between the two indicated atoms and is present or absent, when it is absent y is 2, when it is present y is 1;

—Z— is a one or two atom linker which forms a 5 or 6 member ring Z can be two carbon atoms, a carbon and a sulfur atom, a carbon and a nitrogen, or a carbon and an oxygen, where any remaining valences are satisfied by substitution of atoms with hydrogen or organic substituents, e.g., alkyl groups;

M can be cis or trans with respect to $R^1$; and

M most generally represents a chemical species which is in conjugation with the nitrogen of the core beta-lactam ring system of the compound, such that one or more reactive species, e.g., electrophilic or nucleophilic sites are generated on modification of M which is initiated by cleavage of the beta-lactam ring.

In specific embodiments, R is an aminoacyl group of a known beta-lactam antibiotic. A wide variety of beta-lactam antibiotics is known in the art. Aminoacyl groups of representative known beta-lactam antibiotics are described hereinafter.

Certain M groups of this invention contain good chemical leaving groups which are caused to cleave from the M group by beta-lactam ring cleavage. Beta-lactam cleavage is initiated by attack of a beta-lactamase enzyme on the compound. The reactive groups generated in M on cleavage of the beta-lactam ring are available for reaction with the beta-lactamase and function to inhibit the activity of the beta-lactamase.

Beta-lactam ring systems of the compounds of this invention include those of cephems, cephamycins, carbacephems, penems, and monobactams.

The invention provide compounds of Formula I as generally described above and as more specifically described hereinafter, for use as beta-lactamase inhibitors and beta-lactam antibiotics. Compounds of this invention can exhibit one or both of these functions and as such are useful in a variety of therapeutic (human and veterinary) applications for treatment of microbial infections and complications thereof. The compounds of this invention are particularly useful for treatment of infections of microorganisms, particularly bacteria which are known to exhibit resistance to one or more beta-lactam antibiotics. The compounds of this invention are useful for inhibition of growth of microorganisms including bacteria in vivo or in vitro applications. Beta-lactam inhibitors of this invention may be combined with beta-lactam antibiotics to provide for inhibition of beta-lactamases in vivo or in vivo applications.

Compound of this invention including M groups as described above and in which R is not an aminoacyl group and those in which R is A-CO—NH, where A is an unsubstituted alkyl or aryl group (e.g., phenyl group) are useful as intermediates in the synthesis of beta-lactam inhibitors and beta-lactam antibiotics which exhibit beta-lactamase inhibition and in which the aminoacyl group is that of a known beta-lactam antibiotic. A beta-lactam inhibitor which does not exhibit antibiotic activity or in which it is desired to improve antibiotic activity can be prepared from M group containing compound of this invention by replacing the R group with a selected aminoacyl which is found in a beta-lactam antibiotic which is known in the art. Thus, this invention provides a method for making improved beta-lactam antibiotics which exhibit beta-lactamase inhibition in addition to antibiotic activity.

The invention is further related to pharmaceutical compositions comprising one or more compounds of this invention of formula I and other formulas described herein after.

The invention is also related to method of treatment of infections and related disorders, diseases or complications by administering a therapeutically effective amount or combined amount of one or more compounds of the invention optionally in combination with a therapeutically effective amount or a combined amount of one or more known beta-lactam antibiotics.

The invention is further related to a method of inhibiting the growth of microorganisms, particularly bacteria, by contacting the microorganism in vivo or in vitro with an amount of one or more of the compounds of this invention, optionally in combination with a known beta-lactam antibiotic, particularly an antibiotic that has been used in the past or is currently used for therapeutic applications (in humans or animals).

The invention also relates to method for making medicaments comprising one or more compounds of this invention, particularly for treatment of infections and related disorders, diseases or complications thereof.

The invention is further described and illustrated in the following detailed description, examples and drawings which, however, are not intended to be limiting. Additional, aspects and embodiments of the invention will be apparent on review of the specification as a whole.

BRIEF DESCRIPTION OF THE DRAWINGS

FIG. 3-1 through 3-2 illustrates exemplary acyl groups of compounds of the formulas herein.

FIG. 4-1 through 4-2 illustrates additional exemplary structures of compounds of the invention.

FIG. 5-1 through 5-6 illustrates additional exemplary M groups of the compounds of the invention.

FIG. 6 illustrates preferred stereochemistry of various core beta-lactam ring structures of the formulas of this invention.

DETAILED DESCRIPTION OF THE INVENTION

Figure 1:
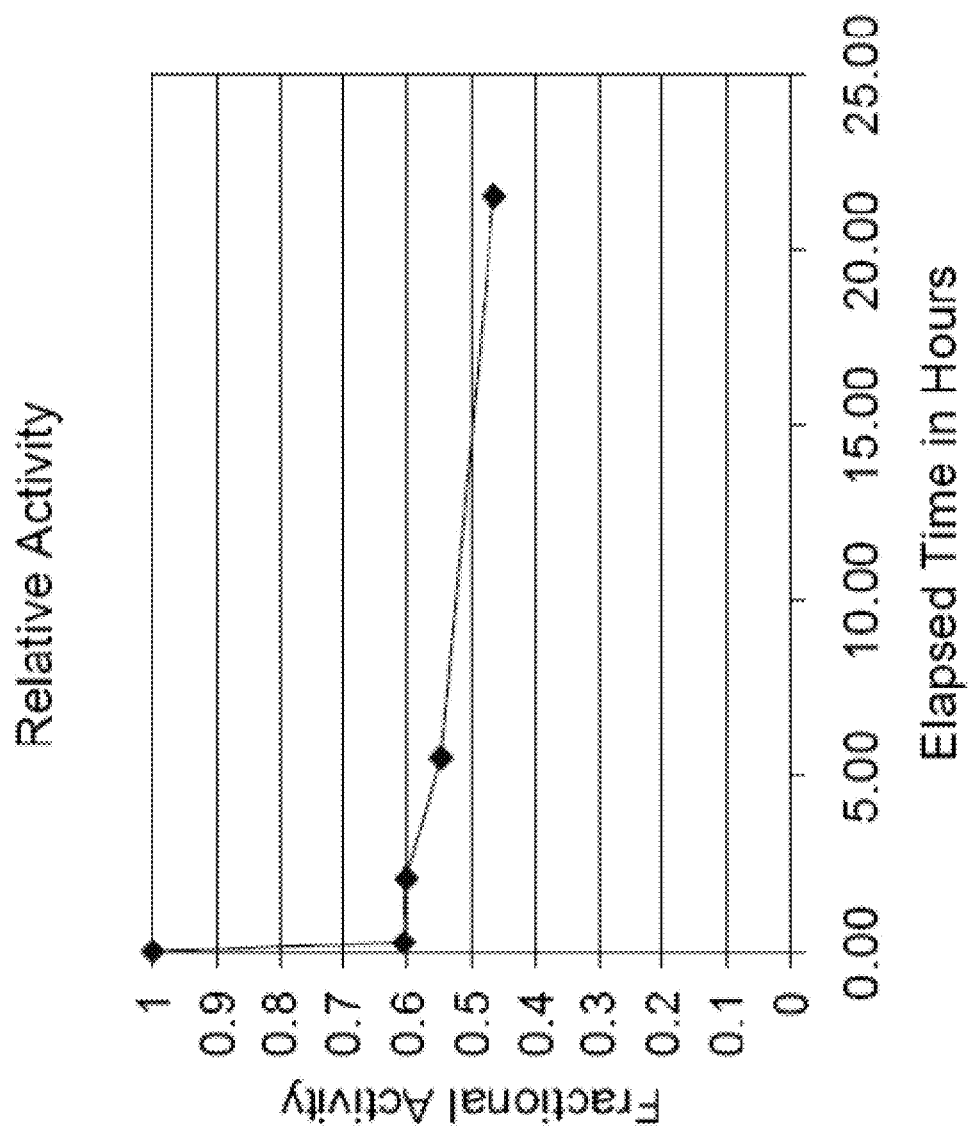
FIG. 1 is a graph of time dependent Inhibition of a beta-lactamase by 3-vinylcyclopropane-7-(2-Phenylacetamido)-3-Cephem-4-carboxylic acid (IX).

The invention relates to methods for making improved beta-lactam antibiotic which exhibit inhibition of one or more beta-lactamases in addition to antibacterial activity. The invention also relates to certain beta-lactam compounds exhibiting inhibition of one or more beta-lactamases. The invention further relates to certain beta-lactam compounds exhibiting beta-lactamase inhibition and antibiotic activity. In specific embodiments, compounds of the invention inhibit one or more beta-lactamases in addition to the Class A penicillinases. In specific embodiments, compounds of the invention inhibit beta-lactamases other than the Class A penicillinases. In specific embodiments, compounds of the invention exhibit inhibition of one or more Class B, C or D beta-lactamases. In specific embodiments, compounds of the invention exhibit broad spectrum inhibition of one or more beta-lactamases of different classes. In specific embodiments, compounds of the invention exhibit irreversible inhibition of one or more beta-lactamases.

In specific embodiments the invention relates to beta-lactam compounds of formula:

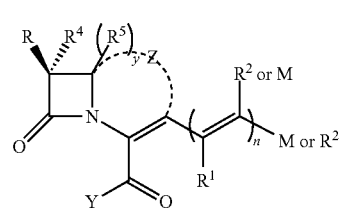

and pharmacologically acceptable salts thereof wherein:
—Z— is present or absent and represents —O—$(CH_2)x$-, —C—$(CH_2)x$-, —NR'—$(CH_2)x$-, —S—$(CH_2)x$-, —SO—$(CH_2)x$-, or —$SO_2$—$(CH_2)x$-, where x is 0 or 1 and R' is hydrogen or C1-C6 alkyl, when —Z— is present y is 1 and when it is absent y is 2;

n is an integer from 1-5;

$R^1$ and $R^2$, independently, are selected from the group consisting of hydrogen, halogen, (C1-C6) alkyl, (C1-C6) alkoxy and (C1-C6) thioalkoxy (—S— alkyl);

Y is O—C+ or $OR^3$ where $R^3$ is hydrogen, or an optionally substituted alkyl or aryl group and C+ is a pharmacologically acceptable cation;

$R^4$ is hydrogen, (C1-C6) alkyl, OR', where R' is hydrogen or (C1-C6) alkyl;

$R^5$ is hydrogen, (C1-C6) alkyl;

R is selected from hydrogen, (C1-C6) alkyl group, (C2-C6) alkenyl group, (C2-C6) alkynyl group, (C7-C19) aralkyl group, a 3-7-member-ring cyclic hydrocarbon group, a 3-7 member heterocyclic group, a (C6-C10) aromatic group, a 6-10 member heterocyclic aromatic group, a —CO—R", —CO2R", —CO—N(R')2; —N(R")2, —NRCO2-R" wherein each R" is independently selected from hydrogen, (C1-C6) alkyl group, (C2-C6) alkenyl group, (C2-C6) alkynyl group, (C7-C19) aralkyl group, a 3-7-member-ring cyclic hydrocarbon group, a 3-7 member heterocyclic group, a (C6-C10) aromatic group, a 6-10 member heterocyclic aromatic group, each of said groups is optionally substituted, and an acylamine group A-CO—NH—; and M, which may be in the cis or trans position with respect to $R^1$, is selected from groups P, B, BZ, D, E, F as follows:

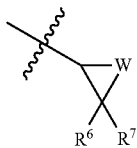

P where:

W is O or C(R") and each R", independently, is selected from the group consisting of hydrogen, halogen, (C1-C6) alkyl group, (C2-C6) alkenyl group, (C2-C6) alkynyl group, (C7-C19) aralkyl group, a 3-7-member-ring cyclic hydrocarbon group, a 3-7 member heterocyclic group, a (C6-C10) aromatic group and a 6-10 member heterocyclic aromatic group wherein each of said groups is optionally substituted; and $R^6$ and $R^7$ are independently selected from hydrogen, halogen, (C1-C6) alkyl group, (C2-C6) alkenyl group, (C2-C6) alkynyl group, (C7-C19) aralkyl group, a 3-7-member-ring cyclic hydrocarbon group, a 3-7 member heterocyclic group, a (C6-C10) aromatic group, a 6-10 member heterocyclic aromatic group, —COR'—, —COOR", —CON(R")$_2$, wherein each R", independently, is selected from the group consisting of hydrogen, halogen, (C1-C6) alkyl group, (C2-C6) alkenyl group, (C2-C6) alkynyl group, (C7-C19) aralkyl group, a 3-7-member-ring cyclic hydrocarbon group, a 3-7 member heterocyclic group, a (C6-C10) aromatic group and a 6-10 member heterocyclic aromatic group and each of said groups is optionally substituted;

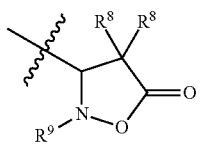

D

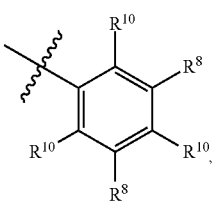

B

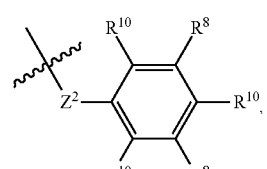

BZ

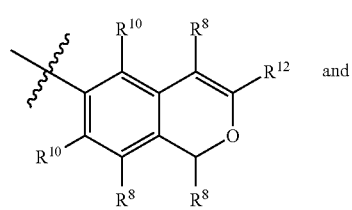

E and

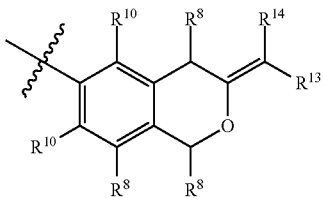

F where:

$Z^2$ is O, $NR^{11}$ or S where $R^{11}$ is selected from the group consisting of hydrogen, (C1-C6) alkyl group, (C2-C6) alkenyl group, and (C2-C6) alkynyl group, where in each group is optionally substituted;

each $R^8$ is independently selected from hydrogen, halogen, (C1-C6) alkyl group, (C2-C6) alkenyl group, (C2-C6) alkynyl group, (C7-C19) aralkyl group, a 3-7-member-ring cyclic hydrocarbon group, a 3-7 member heterocyclic group, a (C6-C10) aromatic group and a 6-10 member heterocyclic aromatic group, a (C1-C6) alkoxy group, a (C1-C6) thioalkyl group, a —CO—R', —CO$_2$R', —CO—N(R')$_2$; —N(R')$_2$, —NR—CO—R', —NRCO$_2$—R' wherein each R' is independently selected from hydrogen, (C1-C6) alkyl group, (C2-C6) alkenyl group, (C2-C6) alkynyl group, (C7-C19) aralkyl group, a 3-7-member-ring cyclic hydrocarbon group, a 3-7 member heterocyclic group, a (C6-C10) aromatic group and a 6-10 member heterocyclic aromatic group, each of said groups is optionally substituted; and each $R^9$ is independently selected from hydrogen, (C1-C6) alkyl group, (C2-C6) alkenyl group, (C2-C6) alkynyl group, (C7-C19) aralkyl group, a 3-7-member-ring cyclic hydrocarbon group, a 3-7 member heterocyclic group, a (C6-C10) aromatic group and a 6-10 member heterocyclic aromatic group wherein each of said groups is optionally substituted;

each $R^{10}$ is independently selected from the group consisting of hydrogen, halogen, (C1-C6) alkyl group, (C2-C6) alkenyl group, (C2-C6) alkynyl group, (C7-C19) aralkyl group, a 3-7-member-ring cyclic hydrocarbon group, a 3-7 member heterocyclic group, a (C6-C10) aromatic group and a 6-10 member heterocyclic aromatic group, a (C1-C6) alkoxy group, a (C1-C6) thioalkyl group, a —CO—R', —CO$_2$R', —CO—N(R')$_2$; —N(R')$_2$, —NR—CO—R', —NRCO$_2$—R' wherein each R' is independently selected from hydrogen, (C1-C6) alkyl group, (C2-C6) alkenyl group, (C2-C6) alkynyl group, (C7-C19) aralkyl group, a 3-7-member-ring cyclic hydrocarbon group, a 3-7 member heterocyclic group, a (C6-C10) aromatic group, a 6-10 member heterocyclic aromatic group wherein each of said groups is optionally substituted, and a —CH$_2$—X group;

$R^{12}$ is selected from the group consisting of hydrogen, (C1-C6) alkyl group, (C2-C6) alkenyl group, (C2-C6) alkynyl group, (C7-C19) aralkyl group, a 3-7-member-ring cyclic hydrocarbon group, a 3-7 member heterocyclic group, a (C6-C10) aromatic group and a 6-10 member heterocyclic aromatic group, a (C1-C6) alkoxy group, a (C1-C6) thioalkyl group, a —CO—R', —CO$_2$R', —CO—N(R')$_2$; —N(R')$_2$, —NR—CO—R', —NRCO$_2$—R' wherein each R' is independently selected from hydrogen, (C1-C6) alkyl group, (C2-C6) alkenyl group, (C2-C6) alkynyl group, (C7-C19) aralkyl group, a 3-7-member-ring cyclic hydrocarbon group, a 3-7 member heterocyclic group, a (C6-C10) aromatic group, a 6-10 member heterocyclic aromatic group, wherein each of said groups is optionally substituted, and X;

$R^{13}$ and $R^{14}$ are independently selected from the group consisting of hydrogen, (C1-C6) alkyl group, (C2-C6) alkenyl group, (C2-C6) alkynyl group, (C7-C19) aralkyl group, a 3-7-member-ring cyclic hydrocarbon group, a 3-7 member heterocyclic group, a (C6-C10) aromatic group and a 6-10 member heterocyclic aromatic group, a (C1-C6) alkoxy group, a (C1-C6) thioalkyl group, a —CO—R', —CO₂R', —CO—N(R')₂; —N(R')₂, —NR—CO—R', —NRCO₂—R' wherein each R' is independently selected from hydrogen, (C1-C6) alkyl group, (C2-C6) alkenyl group, (C2-C6) alkynyl group, (C7-C19) aralkyl group, a 3-7-member-ring cyclic hydrocarbon group, a 3-7 member heterocyclic group, a (C6-C10) aromatic group, a 6-10 member heterocyclic aromatic group wherein each of said groups is optionally substituted, and X; and X is a leaving group as defined below;

wherein in structure V at least one of $R^{10}$ is a —CH₂—X group, $R^{12}$ is X or both; and in structure VI one of $R^{13}$ or $R^{14}$ is X.

In specific embodiments, A-CO— is selected from the group consisting of:

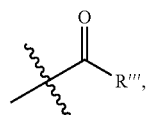
A1

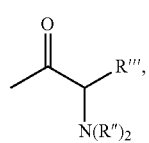
A2

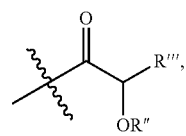
A3

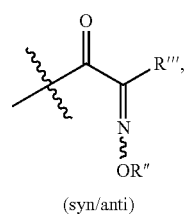
A4
(syn/anti)

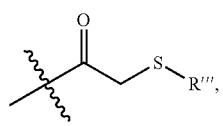
A5

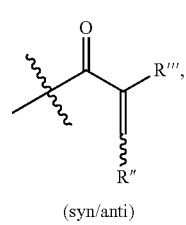
A6
(syn/anti)

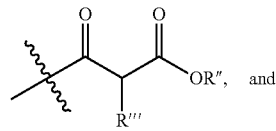
A7

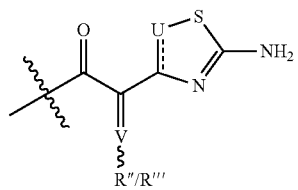
A8 where:

R" for these structures is selected from hydrogen, (C1-C6) alkyl group, (C2-C6) alkenyl group, (C2-C6) alkynyl group, (C7-C19) aralkyl group, a 3-7-member-ring cyclic hydrocarbon group, a 3-7 member heterocyclic group, a (C6-C10) aromatic group and a 6-10 member heterocyclic aromatic group, R'" for these structures is selected from the group consisting of hydrogen, (C1-C6) alkyl group, (C2-C6) alkenyl group, (C2-C6) alkynyl group, (C7-C19) aralkyl group, a 3-7-member-ring cyclic hydrocarbon group, a 3-7 member heterocyclic group, a (C6-C10) aromatic group and a 6-10 member heterocyclic aromatic group, a —CO—R', —CO₂R', —CO—N(R')₂; —N(R')₂, —NR—CO—R', —NRCO₂—R' wherein each R' is independently selected from hydrogen, (C1-C6) alkyl group, (C2-C6) alkenyl group, (C2-C6) alkynyl group, (C7-C19) aralkyl group, a 3-7-member-ring cyclic hydrocarbon group, a 3-7 member heterocyclic group, a (C6-C10) aromatic group, a 6-10 member heterocyclic aromatic group, each of said groups is optionally substituted; and in A8 syn/anti isomers are included, V is N or CH and U is CH, CH₂, NH or N.

In other specific embodiments A-CO— is selected from:

A9

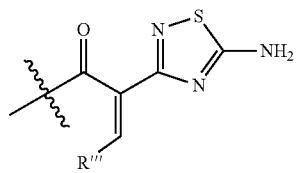
A10

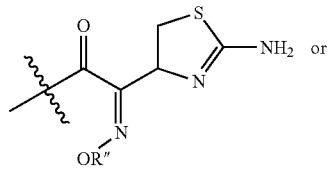
A11 or

-continued

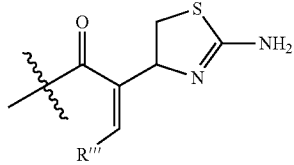

A12 where variables are as defined above.

In other specific embodiments, A-CO— is selected from:

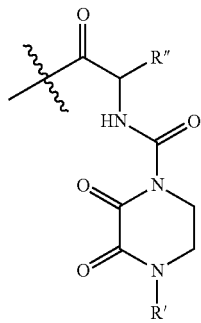

A13

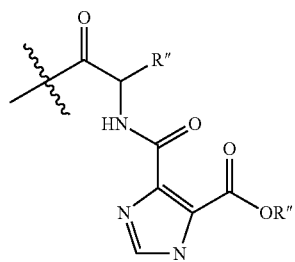

A14 where variables are as defined above.

Figures 2, 3:
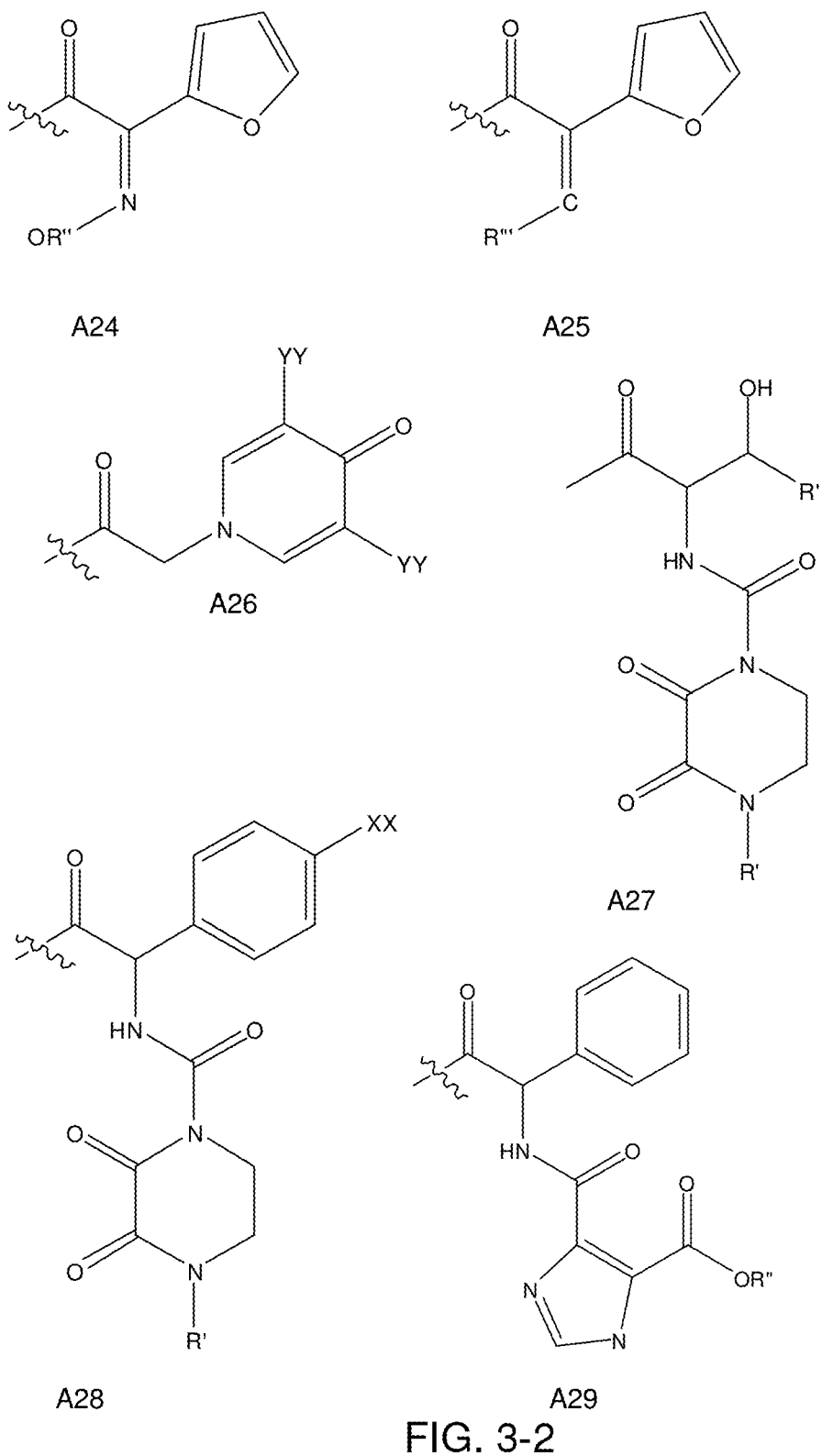

In other specific embodiments, A-CO— is selected from the group consisting of the groups listed illustrated in FIG. 3 (A15-A29) where:

XX is a substituent selected from the group consisting of —OR", —CN, —NH$_2$, —N(R')$_2$, halogen, —SR", —COR''', —COOR", and —CON(R")$_2$;

YY is halogen or —CN;

R' is hydrogen, (C1-C6) alkyl, or (C6-C12) aryl; and

R" and R''' are as defined above under the definition of A groups.

In specific embodiments, XX is OH, YY is Cl, for A24 R' is (C1-C3) alkyl,

In another embodiment, A is a benzyl group or an optionally substituted benzyl group. One or more moieties or groups in the A groups are protected with one or more protecting groups.

In specific embodiments, Y is hydrogen or Y—CO— is an ester that is readily hydrolyzed in vivo.

In another embodiment, the invention provides compounds of formula:

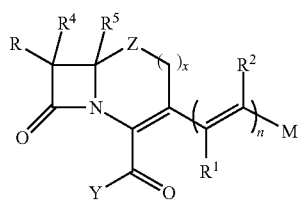

II and pharmaceutically acceptable salts thereof, where variables are as defined above. In specific embodiments, $R^4$ and $R^5$ are both hydrogens. In specific embodiments, R is A-CO—NH—. In specific embodiments, R is benzyl-NH.

In another embodiment, the invention provides compounds of formula:

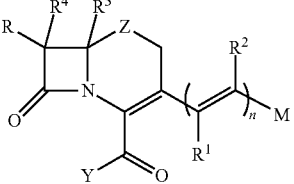

III and pharmaceutically acceptable salts thereof, where variables are as defined above. In specific embodiments, $R^4$ and $R^5$ are both hydrogens. In specific embodiments, R is A-CO—NH—. In specific embodiments, R is benzyl-NH—.

In another embodiment, the invention provides compounds of formula:

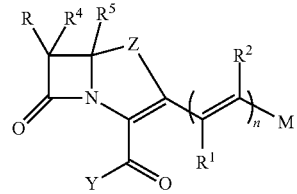

IV and pharmaceutically acceptable salts thereof, where variables are as defined above. In specific embodiments, $R^4$ and $R^5$ are both hydrogens. In specific embodiments, R is A-CO—NH—. In specific embodiments, R is benzyl-NH—.

In another embodiment, the invention provides compounds of formula:

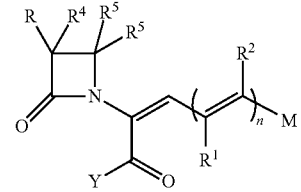

V and pharmaceutically acceptable salts thereof, where variables are as defined above. In specific embodiments, $R^4$ and each $R^5$ is a hydrogen. In specific embodiments, R is A-CO—NH—. In specific embodiments, R is benzyl-NH—. In specific embodiments, $R^{8-10}$ in M groups B, BZ, or F are electron withdrawing groups, including esters, carbamates and alkyl functionalized carbonyl groups.

Figures 1, 5:
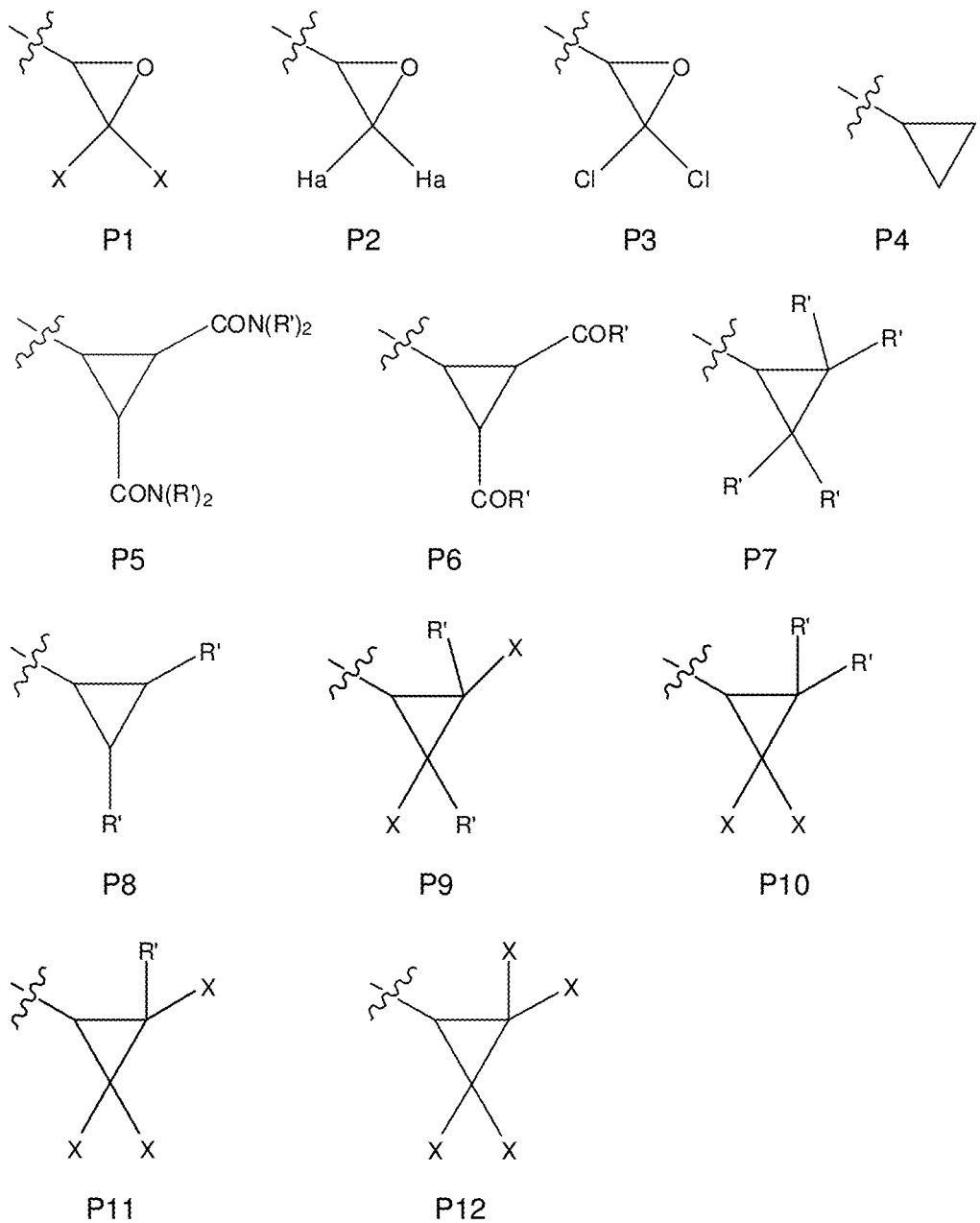
Figures 2, 5:
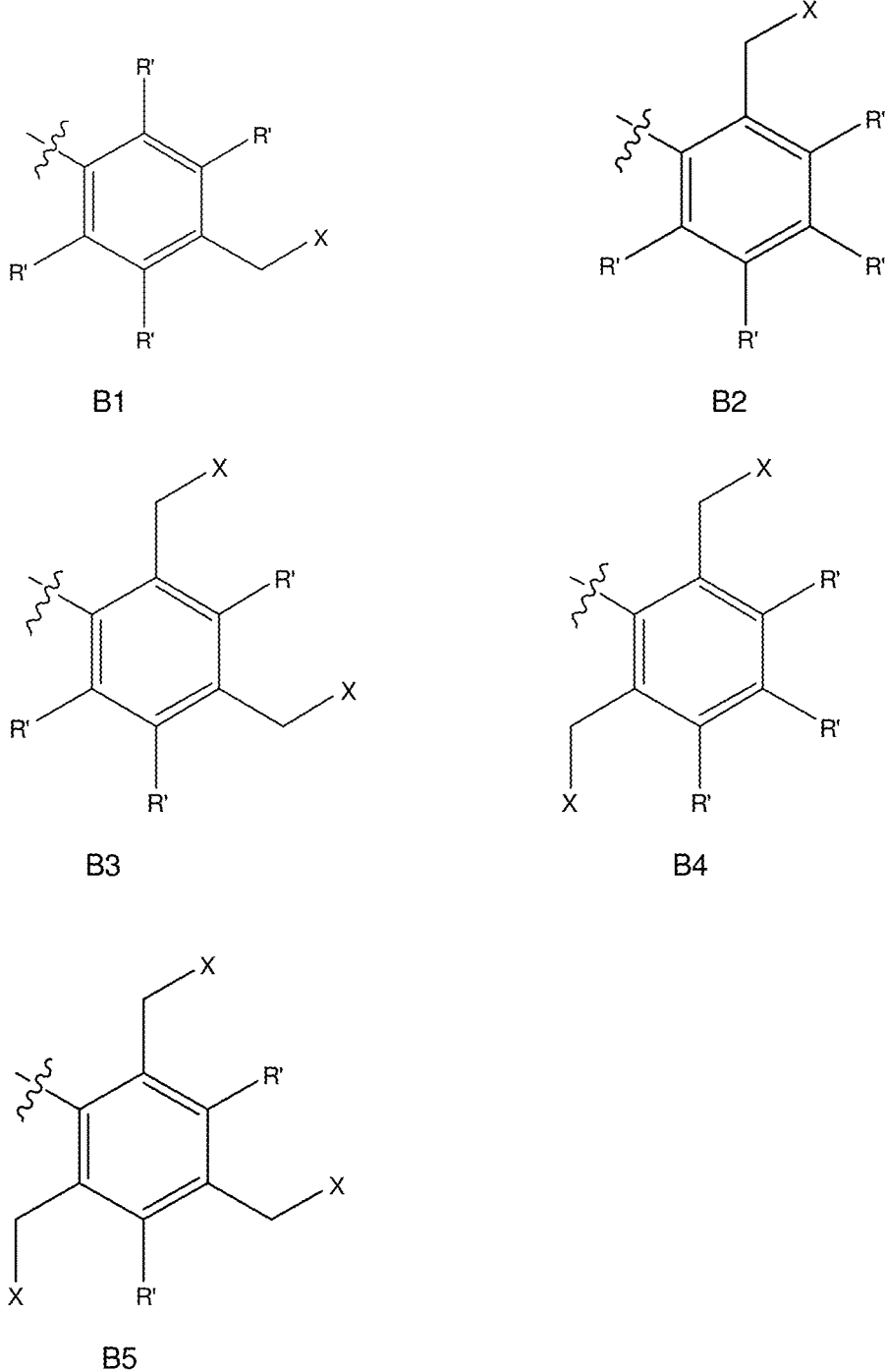
Figures 4, 5:
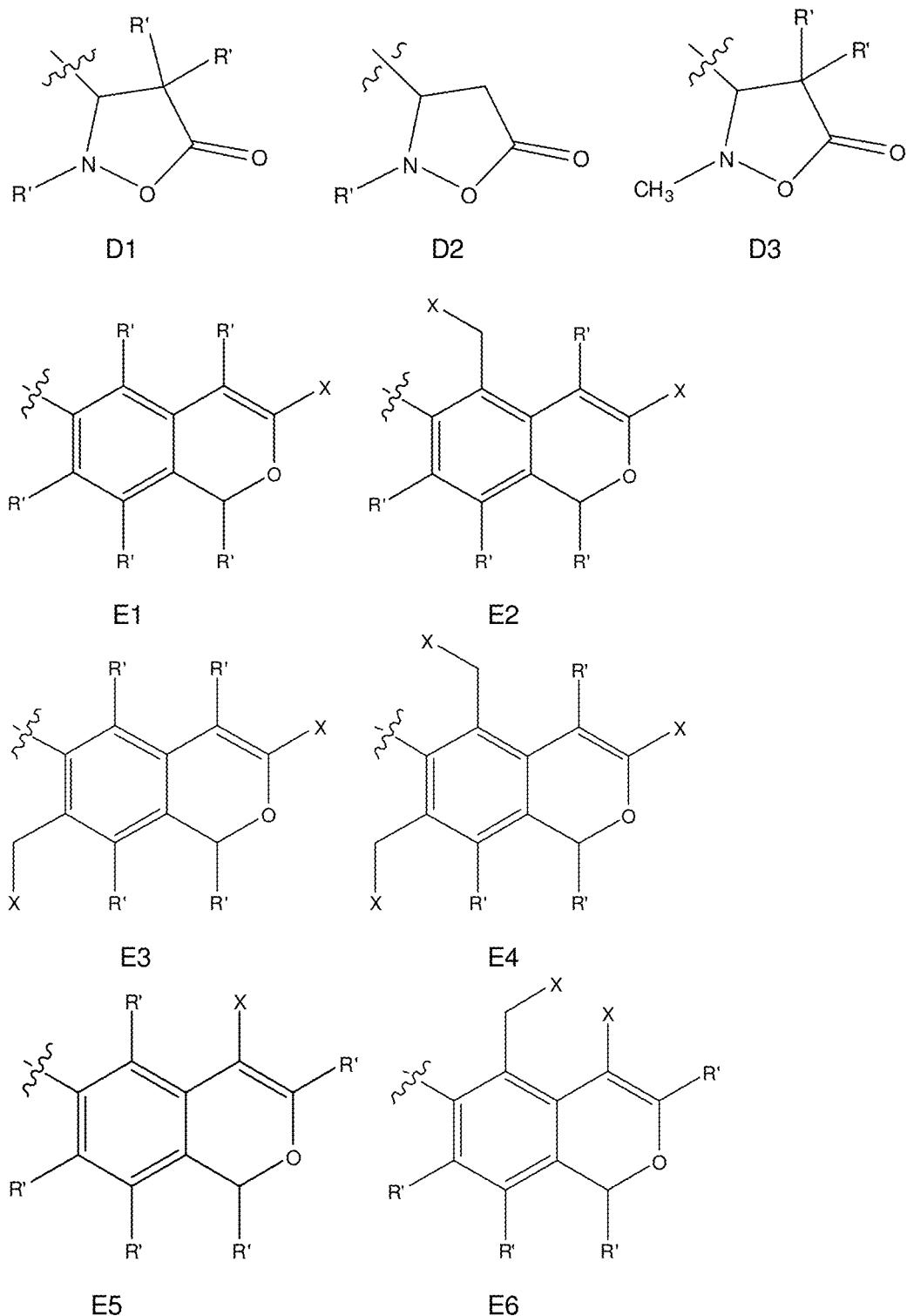
Figure 5:
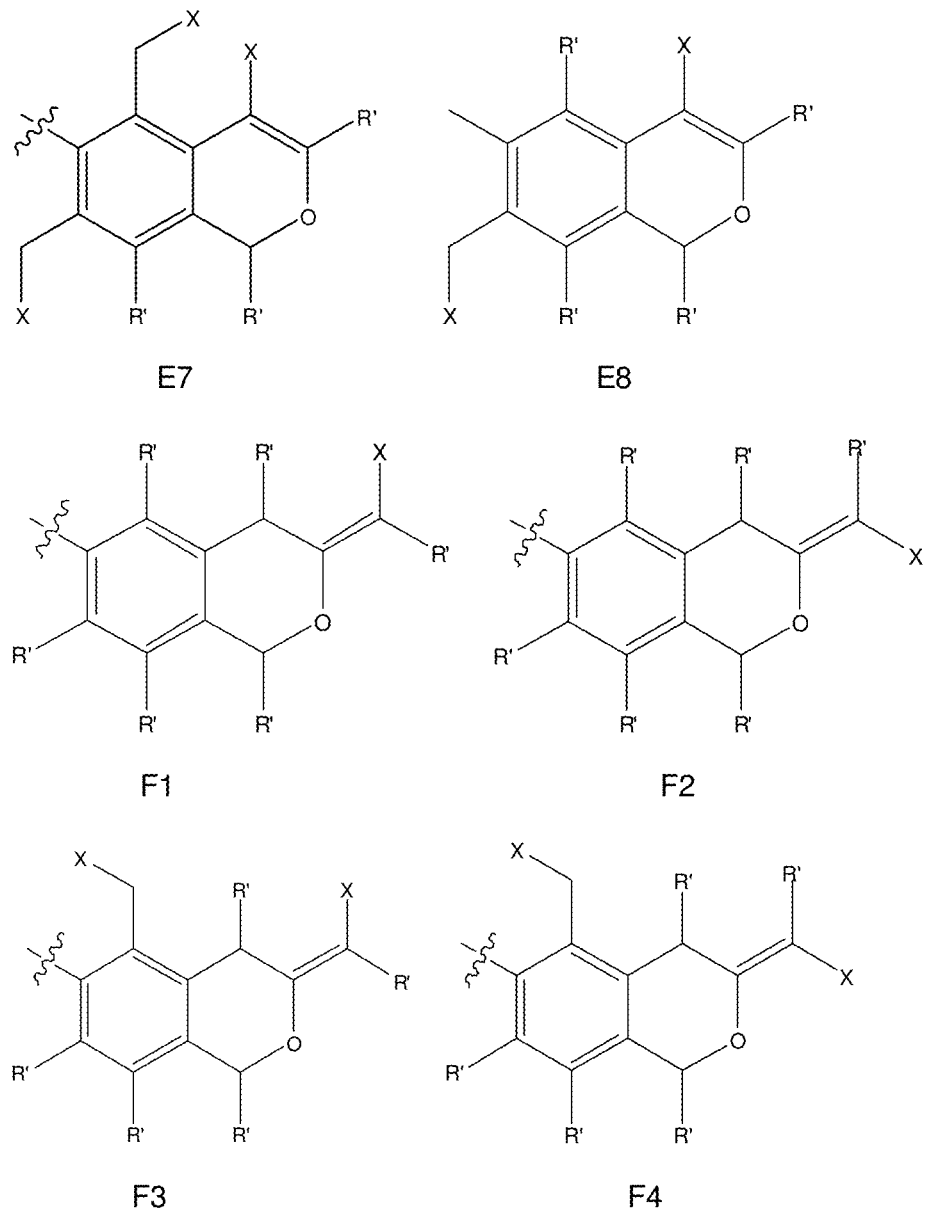

In additional embodiments, the invention provides compounds of formulas C1-C11 as in FIG. 4. In specific embodiments of each of C1-C11, $R^4$ is a hydrogen. In specific embodiments, R is A-CO—NH—. In specific embodiments, R is benzyl-NH—.

In specific embodiments, the invention provides compounds of Formulas S1, S2 and S3 (FIG. 4) where the stereochemistry of certain ring substituents is shown. In specific embodiments, $R^4$ and each $R^5$ is a hydrogen. In specific embodiments, R is A-CO—NH—. In specific embodiments, R is benzyl-NH—, where the benzyl group is optionally substituted. Optional substitution includes substitution with one or more C1-C3 alkyl, C6-C12 aryl, C1-C3 haloalkyl (e.g., —$CF_3$), halogen, I, Cl, Br, F, —OH, or —$NH_2$.

In specific embodiments, the invention provides compounds of any of formulas I, II, III, IV, V, C1-C11, and S1-S3 herein wherein M is selected from one of P1-P12 (FIG. 5), where each Ha, independently, is halogen and X and R' of P1-P12 are as defined above. In specific embodiments, each X, independently, is a good leaving group as defined herein. In specific embodiments, each Ha, independently, is I, Br or Cl. In specific embodiments, each X is Cl. In specific embodiments, each X is Br. In specific embodiments, each X is a pyridinium group. In specific embodiments, one X is a pyridinium group. In specific embodiments, each R', independently, is hydrogen, C1-C6 alkyl, or C6-C12 aryl, both of which are optionally substituted. In specific embodiments, each R', independently, is hydrogen or C1-C3 alkyl which is optionally substituted. In specific embodiments, each R' is hydrogen. In specific embodiments, all X are the same. Optional substitution includes substitution with one or more C1-C3 alkyl, C6-C12 aryl, C1-C3 haloalkyl (e.g., —$CF_3$), halogen, I, Cl, Br, F, —OH, or —$NH_2$.

In specific embodiments, the invention provides compounds of any of formulas I, II, III, IV, V, C1-C11, and S1-S3 wherein M is selected from one of B1-B5 (FIG. 5), where X and R' of the B1-B5 are as defined above. In specific embodiments, each X, independently, is a good leaving group as defined herein. In specific embodiments, each X, independently, is I, Br or Cl. In specific embodiments, each X is Cl. In specific embodiments, each X is Br. In specific embodiments, each X is a pyridinium group. In specific embodiments, each R', independently, is hydrogen, C1-C6 alkyl, or C6-C12 aryl, both of which are optionally substituted. In specific embodiments, each R', independently, is hydrogen or C1-C3 alkyl which is optionally substituted. In specific embodiments, each R' is hydrogen. In specific embodiments, all X are the same. In specific embodiments, two X are the same. Optional substitution includes substitution with one or more C1-C3 alkyl, C6-C12 aryl, C1-C3 haloalkyl (e.g., —$CF_3$), halogen, I, Cl, Br, F, —OH, or —$NH_2$.

In specific embodiments, the invention provides compounds of any of formulas I, II, III, IV, V, C1-C11, and S1-S3 wherein M is selected from one of BZ1-BZ5 (FIG. 5), where X and R' of the BZ1-BZ5 are as defined above. In specific embodiments, each X, independently, is a good leaving group as defined herein. In specific embodiments, each X, independently, is I, Br or Cl. In specific embodiments, each X is Cl. In specific embodiments, each X is Br. In specific embodiments, each X is a pyridinium group. In specific embodiments, each R', independently, is hydrogen, C1-C6 alkyl, or C6-C12 aryl, both of which are optionally substituted. In specific embodiments, each R', independently, is hydrogen or C1-C3 alkyl which is optionally substituted. In specific embodiments, each R' is hydrogen. In specific embodiments, all X are the same. In specific embodiments, two X are the same. Optional substitution includes substitution with one or more C1-C3 alkyl, C6-C12 aryl, C1-C3 haloalkyl (e.g., —$CF_3$), halogen, I, Cl, Br, F, —OH, or —$NH_2$.

In specific embodiments, the invention provides compounds of any of formulas I, II, III, IV, V, C1-C11, and S1-S3 wherein M is selected from one of D1-D3 (FIG. 5), where R' of D1-D3 is as defined above. In specific embodiments, each R', independently, is hydrogen, C1-C6 alkyl, or C6-C12 aryl, both of which are optionally substituted. In specific embodiments, each R', independently, is hydrogen or C1-C3 alkyl which is optionally substituted. In specific embodiments, each R' is hydrogen. In specific embodiments, all R' are the same.

In specific embodiments, the invention provides compounds of any of formulas I, II, III, IV, V, C1-C11, and S1-S3 wherein M is selected from one of E1-E8 (FIG. 5), where X and R' of E1-E8 are as defined above. In specific embodiments, each X, independently, is a good leaving group as defined herein. In specific embodiments, each X, independently, is I, Br or Cl. In specific embodiments, each X is Cl. In specific embodiments, each X is Br. In specific embodiments, each X is a pyridinium group. In specific embodiments, each R', independently, is hydrogen, C1-C6 alkyl, or C6-C12 aryl, both of which are optionally substituted. In specific embodiments, each R', independently, is hydrogen or C1-C3 alkyl which is optionally substituted. In specific embodiments, each R' is hydrogen. In specific embodiments, all X are the same. In specific embodiments, two X are the same. In specific embodiments, X directly bonded to the ring is different from X indirectly bonded to the ring. In specific embodiments, X directly bonded to the ring is a halogen and the X indirectly bonded to the ring is not a halogen. Optional substitution includes substitution with one or more C1-C3 alkyl, C6-C12 aryl, C1-C3 haloalkyl (e.g., —$CF_3$), halogen, I, Cl, Br, F, —OH, or —$NH_2$.

In specific embodiments, the invention provides compounds of any of formulas I, II, III, IV, V, C1-C11, and S1-S3 wherein M is selected from one of F1-F8 (FIG. 5), where X and R' of F1-F8 are as defined above. In specific embodiments, each X, independently, is a good leaving group as defined herein. In specific embodiments, each X, independently, is I, Br or Cl. In specific embodiments, each X is Cl. In specific embodiments, each X is Br. In specific embodiments, each X is a pyridinium group. In specific embodiments, one X is a pyridinium group. In specific embodiments, each R', independently, is hydrogen, C1-C6 alkyl, or C6-C12 aryl, both of which are optionally substituted. In specific embodiments, each R', independently, is hydrogen or C1-C3 alkyl which is optionally substituted. In specific embodiments, each R' is hydrogen. In specific embodiments, all X are the same. In specific embodiments, two X are the same. In specific embodiments, X directly bonded to the ring is different from X indirectly bonded to the ring. In specific embodiments, X directly bonded to the ring is a halogen and the X indirectly bonded to the ring is not a halogen. Preferred substituents for optional substitution includes among others substitution with one or more C1-C3 alkyl, C6-C12 aryl, C1-C3 haloalkyl (e.g., —$CF_3$), halogen, I, Cl, Br, F, —CN, —OH, C1-C3 alkoxy, —O-aryl, —O-benzyl, -phenoxy, —SH, —SR (where R is C1-C3 alkyl, benzyl or phenyl), —$NH_2$, —$N(R)_2$ (where each R is C1-C3 alkyl, benzyl or phenyl). Alkyl, aryl, benzyl, phenyl groups of these substituents are in turn optionally substituted.

In specific embodiments, isomers of the compounds of formulas II-V, C1-C11, and S1-S3 in which the M group is cis to the $R^1$ group are also provided.

In specific embodiments, the compounds of formula I exclude cefprozil, cefdinir, cefditoren, cefixime, and ceftobiprole. However, other compounds of formula I maybe combined with one or more of cefprozil, cefdinir, cefditoren, cefixime, or ceftobiprole in pharmaceutical compositions or in medicaments.

Figure 6:
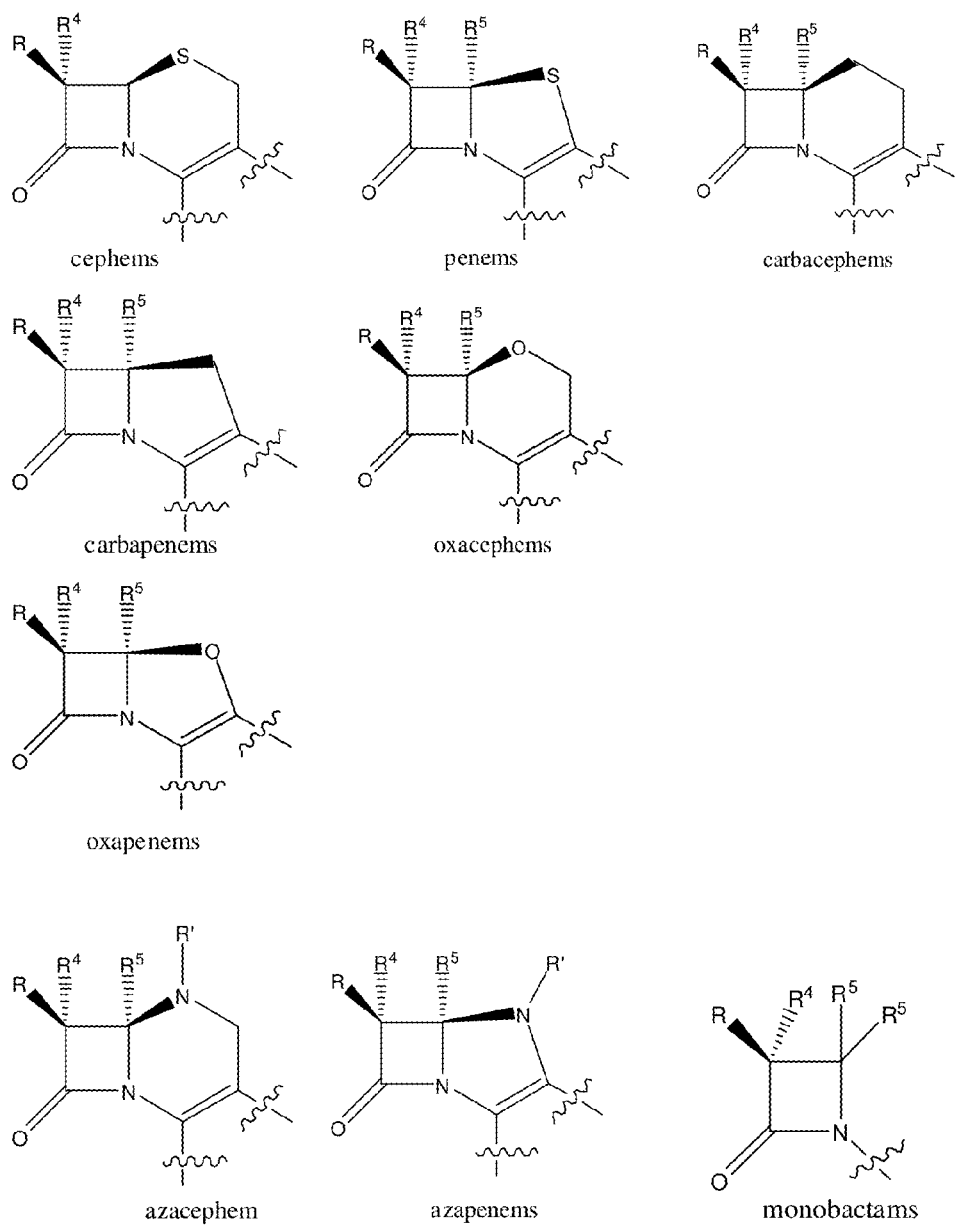

FIG. 6 illustrates preferred stereochemistry of various core beta-lactam structures of the formulas of this invention. In specific embodiments, compounds of the invention include those of any formula herein which also have the illustrated preferred stereochemistry in FIG. 6.

The term "alkyl" refers to a monoradical of a branched or unbranched (straight-chain or linear) saturated hydrocarbon and to cycloalkyl groups having one or more rings. Unless otherwise indicated preferred alkyl groups have 1 to 22 (C1-C22) carbon atoms and more preferred are those that contain 1-12 carbon atoms (C1-12). Short alkyl groups are those having 1 to 6 carbon atoms and those having 1-3 carbon atoms (C1-C3), including methyl, ethyl, propyl, butyl, pentyl and hexyl groups, including all isomers thereof. Long alkyl groups are those having 8-30 carbon atoms and preferably those having 12-22 carbon atoms (C12-C22). The term "cycloalkyl" refers to cyclic alkyl groups having preferably 3 to 12 (C3-C12) carbon atoms having a single cyclic ring or multiple condensed rings. Descriptions herein with respect to alkenyl groups apply generally to cycloalkenyl groups. Cycloalkyl groups include, by way of example, single ring structures such as cyclopropyl, cyclobutyl, cyclopentyl, cyclohexyl, cyclooctyl, and the like, or multiple ring structures such as adamantanyl, and the like. Unless otherwise indicated alkyl groups including cycloalkyl groups are optionally substituted as defined below.

The term "alkenyl" refers to a monoradical of a branched or unbranched unsaturated hydrocarbon group having one or more double bonds and to cycloalkenyl groups having one or more rings wherein at least one ring contains a double bond. Unless otherwise indicated alkyl groups have 2 to 22 carbon atoms (C2-22) and more preferred are those that contain 2-12 carbon atoms (C2-12). Alkenyl groups may contain one or more double bonds (C=C) which may be conjugated or unconjugated. Preferred alkenyl groups as substituents are those having 1 or 2 double bonds and include omega-alkenyl groups. Alkenyl groups can contain 2-5, 4, 3, or 2 conjugated double bonds. Alkenyl groups include those having 2 to 6 carbon atoms (C2-C6) and those having 2-3 carbon atoms (C2-C3), including ethylene (vinyl), propylene, butylene, pentylene and hexylene groups including all isomers thereof. The term "cycloalkenyl" refers to cyclic alkenyl groups of from 3 to 22 carbon atoms (C3-C22) having a single cyclic ring or multiple condensed rings in which at least one ring contains a double bond (C=C). Descriptions herein with respect to alkenyl groups apply generally to cycloalkenyl groups. Cycloalkenyl groups preferably have 3-12 carbon atoms (C3-C12). Cycloalkenyl groups include, by way of example, single ring structures (monocyclic) such as cyclopropenyl, cyclobutenyl, cyclopentenyl, cyclohexenyl, cyclooctenyl, cylcooctadienyl and cyclooctatrienyl as well as multiple ring structures. Unless otherwise indicated alkenyl groups including cycloalkenyl groups are optionally substituted as defined below.

The term "alkynyl" refers to a monoradical of an unsaturated hydrocarbon having one or more triple bonds (C≡C). Unless otherwise indicated preferred alkyl groups have 2 to 22-carbon atoms and more preferred are those that contain 2-12 carbon atoms. Alkynyl groups include ethynyl, propargyl, and the like. Short alkynyl groups are those having 2 to 6 carbon atoms (C2-C6) and those including 2 or 3 carbon atoms (C2-C3), including all isomers thereof. Longer alkynyl groups are those having 6-12 carbon atoms (C6-C12). The term "cycloalkynyl" refers to cyclic alkynyl groups of from 3 to 22 (C3-C22) carbon atoms having a single cyclic ring or multiple condensed rings in which at least one ring contains a triple bond (C≡C). Descriptions herein with respect to alkynyl groups apply generally to cycloalkynyl groups. Unless otherwise indicated alkynyl groups including cycloalkynyl groups are optionally substituted as defined below.

The term "aryl" refers to a chemical group containing an unsaturated aromatic carbocyclic group of from 6 to 22 carbon atoms (C6-C22) having a single ring (e.g., phenyl), one or more rings (e.g., biphenyl) or multiple condensed (fused) rings, wherein at least one ring is aromatic (e.g., naphthyl, dihydrophenanthrenyl, fluorenyl, or anthryl). An aryl group is formally formed by removal of a hydrogen from an aryl compound. Aryls include phenyl, naphthyl and the like. Aryl groups contain may contain portions that are alkyl, alkenyl or alkynyl in addition to the unsaturated aromatic ring(s). The term "alkaryl" refers to the aryl groups containing alkyl portions, i.e., -alkylene-aryl and -substituted alkylene-aryl. Such alkaryl groups are exemplified by benzyl, phenethyl and the like.

The term "heterocyclyl" generically refers to a monoradical that contains at least one ring of atoms, typically a 3-10 member ring, preferably a 5, 6 or 7 member ring which may be a saturated or unsaturated ring (e.g., containing double bonds) wherein the ring can contain one or more carbon atoms and one or more heteroatoms (a non-carbon atom). Heterocyclic groups can contain 1, 2 or 3 rings (2 or more rings can be designated a ring system) at least one of which is a heterocyclic ring. To satisfy valence the heteroatom may be bonded to H or a substituent group. Ring carbons may be replaced with —O—, —S—, —NR—, —N=, among others, where R in this definition is hydrogen or an alkyl, aryl, heterocyclyl or heteroaryl group. Several heterocyclic groups, rings and ring systems are more specifically described in the specification hereof.

The term "heteroaryl" refers to a group that contains at least one aromatic ring (typically a 5 or 6-member ring) in which one or more of the ring carbons is replaced with a heteroatom (non-carbon atom). To satisfy valence the heteroatom may be bonded to H or a substituent group. Ring carbons may be replaced with —O—, —S—, —NR—, —N=, among others, where R in this definition is hydrogen or an alkyl, aryl, heterocyclyl or heteroaryl group. Heteroaryl groups may include one or more aryl groups (all-carbon aromatic rings) or heteroaryl rings and aryl rings of the heteroaryl group may be linked by a single bond or a linker group (e.g., alkylene $(CH_2)_n$) or may be fused. Heteroaryl groups include those having aromatic rings with 5 or 6 ring atoms of which 1-3 ring atoms are heteroatoms. Preferred heteroatoms are —O—, —S—, —NR— and —N=. Heteroaryl groups include those containing 5-12 carbon atoms. Unless otherwise noted heteroaryl groups are optionally substituted as described herein.

"Haloalkyl" refers to alkyl as defined herein substituted by one or more halo groups as defined herein, which may be the same or different. Representative haloalkyl groups include, by way of example, perfluoroalkyl groups, trifluoromethyl, difluoromethyl, chloromethyl, bromomethyl, chloro-ethyl, bromo-ethyl, chloro-cyclopropyl, 2,3-dichlorocyclopropyl, and the like. Haloalkyl groups include those having 1-6 (C1-C6) and 1-3 (C1-C3) carbon atoms and which contain 1, 2, 3, 5, 7, 9, 11, 13 (e.g., perchloro groups), 1-6 or 1-13 halogens. Halogens include among others, chlorine, bromine, iodine and fluorine. In certain embodiments, chlorine, bromine and iodine are preferred halogens.

The term "haloaryl" similarly refers to an aryl group as defined herein substituted by one or more by one or more halo groups as defined herein, which may be the same or different. Representative haloaryl groups include among others para-halophenyl, ortho-halophenyl, meta-halophenyl, and phenyl rings carrying combinations of 2-5 halogens at ortho, meta, para positions or combinations thereof. Haloaryl groups include those having 6 or 12 carbon atoms (C6 or C12) which can carry 1-5 or 1-9 halogens. Haloaryls include perhalogenated aryl groups. Halogens include among others, chlorine, bromine, iodine and fluorine. In certain embodiments, chlorine, bromine and iodine are preferred halogens.

The term alkoxy (or alkoxide) refers to a —O-alkyl group, where alkyl groups are as defined above. The term alkenoxy (alkenoxide) refers to a —O-alkenyl group where alkenyl groups are as defined above wherein the double bond can in certain embodiments be positioned at the carbon bonded to the oxygen. In most substituents that are alkeneoxy groups the double bond is preferably not positioned at the carbon bonded to the oxygen. The term alkynoxy (alkynoxide) refers to a —O-alkynyl group where alkynyl groups are as defined above and wherein a triple bond is preferably not positioned at the carbon bonded to the oxygen. The term aryloxy, refers to an —O-aryl group. The term heteroaryloxy, refers to an —O-heteroaryl group. The term heterocyclyloxy, refers to an —O-heterocyclyl group.

The term "amino" refers generically to a —N(R)$_2$ group wherein R for this definition and independently of other R is hydrogen, alkyl, alkenyl, alkynyl, aryl, heterocyclyl, or heteroaryl radical as described above. Two of R may be linked to form a ring. An "alkyl amino" group refers to an amino group wherein at least one R is alkyl. An "aryl amino" group refers to an amino group wherein at least one R is aryl.

The term "amido" refers generically to an —CO—N—(R)$_2$ group wherein R, for this definition, independently of other R, is hydrogen, alkyl, alkenyl, alkynyl, aryl, heterocyclyl, or heteroaryl radical as described above. Two of R may be linked to form a ring. An "alkyl amido" group refers to an amido group wherein at least one R is alkyl. An "aryl amido" group refers to an amido group wherein at least one R is aryl.

The term "aminoacyl" group" refers generically to an —NR—CO—R group wherein, for this definition, each R independently is hydrogen, alkyl, alkenyl, alkynyl, aryl, heterocyclyl, or heteroaryl radical as described above. An "alkyl aminoacyl" group refers to an aminoacyl group wherein at least one R is alkyl. An "aryl amido" group refers to an aminoacyl group wherein at least one R is aryl. A variety of amino acyl group are more specifically described in the specification hereof.

The term "imine" refers generically to an —N=CR"$_2$ group or an —CR"=NR" group wherein in this definition each R" independently of other R" is hydrogen, alkyl, alkenyl, alkynyl, aryl, heterocyclyl, or heteroaryl radical as described above. Two of R" may be linked to form a ring. An "alkyl imine" group refers to an imine group wherein at least one R" is alkyl. An "aryl imine" group refers to an imine group wherein at least one R" is aryl. Several imine groups are more specifically described in the specification hereof.

The term "sulfenyl" refers to the radical —S—R where R, in this definition, is an alkyl, alkenyl, alkynyl, aryl, heterocyclyl, or heteroaryl radical as described above. The term "sulfhydryl" refers to the —SH group.

The term "sulfonyl" refers to the radical —SO$_2$—R where R, in this definition, is an alkyl, alkenyl, alkynyl, aryl, heterocyclyl, or heteroaryl radical as described above.

The term "sulfonate" refers to the radical —SO$_3$—R where R, in this definition, is hydrogen, alkyl, alkenyl, alkynyl, aryl, heterocyclyl, or heteroaryl radical as described above. An "alkyl sulfonate" group refers to a sulfonate group wherein R is alkyl. An "aryl sulfonate" group refers to an sulfonate group wherein at least one R is aryl. The group —SO$_3$H can be in the ionic form —SO$_3^-$.

Alkyl, alkenyl, alkynyl, aryl, heteroaryl, and heterocyclic groups or the alkyl, alkenyl, alkynyl, aryl, heteroaryl, and heterocyclic portions of groups are optionally substituted (unless noted otherwise) as described herein and may contain 1-8 non-hydrogen substituents dependent upon the number of carbon atoms in the group and the degree of unsaturation of the group. Alkyl, alkenyl, alkynyl, aryl, heteroaryl, and heterocyclic groups may also be unsubstituted.

Optional substitution refers to substitution with one or more of the following functional groups (hydrogen is not herein considered to be a functional group):

Halogens, hydroxyl (—OH), —CN, —SH, alkyl, alkenyl, alkynyl, aryl, heterocyclyl, heteroaryl, alkoxy, alkenoxy, alkynoxy, aryloxy, heteroaryloxy, heterocyclyloxy, sulfenyl, sulfonyl, sulfonate, amine, amido, aminoacyl, imine, —COR, —COOR, —CON(R)$_2$, —OCOR, —OCOR, —OCN(R)$_2$, haloalkyl, haloalkenyl, haloaryl, —CO—C(R)$_2$—CO—, —NRCOR, —NRCOOR, —COO$^-$C$^+$, where each R in this definition is selected from hydrogen, alkyl, alkenyl, alkynyl, aryl, heterocyclyl, heteroaryl, (which in turn are optionally substituted) and C$^+$ is a pharmaceutically acceptable cation (of a pharmaceutically acceptable salt).

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

The compounds of this invention may contain one or more chiral centers. Accordingly, this invention is intended to include racemic mixtures, diasteromers, enantiomers and mixture enriched in one or more steroisomer. The scope of the invention as described and claimed encompasses the racemic forms of the compounds as well as the individual enantiomers and non-racemic mixtures thereof.

The compounds of the present inventions form salts which are also within the scope of this invention. Reference to a compound of the formulas (I-V) herein is understood to include reference to salts thereof, unless otherwise indicated. The term "salt(s)", as employed herein, denotes acidic and/or basic salts formed with inorganic and/or organic acids and bases. In addition, when a compound contains both a basic moiety, such as, but not limited to an amine or a pyridine ring, and an acidic moiety, such as, but not limited to, a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, cam phorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Compounds of the present invention, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore exist in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

The invention also relates to prodrug forms of the compounds of formulas I-V herein. The term "prodrug" refers to an agent that is converted into the parent drug in vivo. A prodrug is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. Prodrugs may be easier to administer than the parent drug in some situations. For example, the prodrug may be bioavailable by oral administration but the parent is not, or the prodrug may improve solubility to allow for intravenous administration. Knowledge of pharmacodynamic processes and drug metabolism in vivo, allows those of ordinary skill in the art, once a pharmaceutically active compound is known, can design prodrugs of the compound. Various forms of prodrugs are well known in the art. For examples of such prodrug derivatives. [see: Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191 (1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392.]

Leaving groups are typically substituents which are able to leave as a stable, weakly basic species. In some cases, leaving groups leave as anions, in other they leave as neutral molecules. A "good leaving group" can be recognized as being the conjugate base of a strong acid. Good leaving groups include, among others, halogens, particularly I, Br, and Cl, —CC(O)R', —SC(O)R', —OCOR', thiol (—SH), sulfenyl (—SR'), phenoxy, pentafluorphenoxy, tosyl and tosyl variants including p-fluorotosyl, p-bromotosyl, p-nitrobenzyltosyl, pentafluorotosyl, where R' for this definition can be selected from optionally substituted alkyl and aryl groups, specific R' include C1-C3 alkyls, particularly methyl groups, or pyridinium groups:

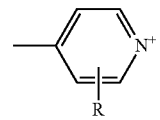

where R, in this definition, represents hydrogens or 1-5 non-hydrogen groups, which include, among others, C1-C3 alkyl groups. Leaving groups as used herein further include species like cyclopropyl groups, including substituted cyclopropyl groups, in which the bond breaking of the "leaving" involves ring opening. In this case, ring strain generated upon change in hybridization and electron withdrawing properties cause the cyclopropyl ring to open.

The term beta-lactam antibiotic is used broadly herein to refer to any compound recognized in the art as containing a beta-lactam ring structures, including for example those ring structures illustrated in FIG. 6, and which exhibits antibiotic activity against one or more microorganisms, particularly bacteria. Beta-lactam antibiotics include those described in the following references: Queener et al. *Beta-lactam Antibiotics for Clinical Use* 1986 (Informa Health Care); and Mitsuhashi *Beta-lactam Antibiotics* 1981 (Japan Scientific Societies Press).

Beta-lactam compound is most generally a compound which comprises a beta-lactam ring, see exemplary rings in FIG. 4-1 through 4-2 and FIG. 6. Beta-lactam compounds of interest in this invention are those which exhibit antibiotic activity and/or inhibition of one or more beta-lactamases and preferably those that exhibit both activities.

The term beta-lactamases is used broadly herein to refer to enzymes from any sources which catalyze beta-lactam ring opening. Beta-lactamases (EC 3.5.2.6) are enzymes most commonly produced by bacteria. Beta-lactamases catalyze the hydrolytic ring opening of beta-lactam rings and are responsible for conferring bacterial resistance to beta-lactam antibiotics such as penicillins, penams, penems, cephems, cephalosporins, carbacephems, cephamycins, and monobactams. Some beta-lactamases have evolved to thermodynamic perfection wherein diffusion of beta-lactam to beta-lactamase is the rate determining step. Many different classification systems have been used to categorize beta-lactamases including genetic and mechanistic schemes. At the simplest level beta-lactamases can be divided up into two categories. Serine hydrolases catalyze their reactions through the use of an active site serine that is acylated during the reaction in a Ping-Pong-Bi-Bi mechanism if water is accounted as a substrate or Uni-Bi-Bi if the solvent water molecules are ignored. Metallo beta-lactamases catalyze hydrolysis of the amide bond of the lactam ring via direct nucleophilic attack of a water molecule using one or two $Zn^{++}$ ions. This Bi-Bi mechanism if water is counted or Uni-Bi mechanism if water is ignored does not proceed through an acyl enzyme intermediate.

Beta-lactamase inhibitor is also used broadly herein to refer to chemical species, particularly small molecules (e.g., molecules other than peptides or proteins). Beta-lactamases can be inhibited by small molecules via reversible competitive, noncompetitive, uncompetitive, and slow tight binding mechanisms as well as irreversible active-site-directed and mechanism based or suicide mechanisms. Such inhibitor molecules decrease the catalytic rate of beta-lactamase reactions or completely prevent beta-lactamases from performing any catalysis at all. Examples of reversible competitive inhibitors include boronic acids. Examples of active-site-directed irreversible inhibitors include phosphate or phosphonate esters. Examples of mechanism based inhibitors include clavulanic acid, sulbactam and tazobactam.

Beta-lactam compounds of interest in this invention are those which exhibit inhibition of one or more beta-lactamases and preferably those that exhibit both activities and/or antibiotic activity. Beta-lactamase inhibitors of this invention, do not include clavulanic acid, sulbactam and tazobactam, however, one or more compounds of this invention can be combined with one or more of these known inhibitors in pharmaceutical compositions or medicaments.

Compounds of this invention can be synthesized employing methods as described herein or using routine adaptations of these methods with art-known or commercially available starting materials and reagents in view of what is generally known in the art with respect to the synthesis of the various classes of known beta-lactam inhibitors and known beta-lactam antibiotics. For example, synthesis of starting materials for synthesis of compounds of the invention and also in the synthesis of compounds of the invention may be achieved using well-known methods and readily available materials, such as provided in March; Larock, *Comprehensive Organic Transformations* (VCH Publishers, 1989); Larock *Comprehensive Organic Transformations: A Guide to Functional Group Preparations*, Second Edition, (John Wiley & Sons, Inc., 1999); Smith, March *March's Advanced Organic Chemistry: Reactions, Mechanisms, and Structure*, Sixth Edition, (John Wiley & Sons, Inc., 2007); G. I. Georg, *The Organic Chemistry Of .Beta.-Lactams*, (VCH 1992), Page *Chemistry of Beta-Lactams* (Springer, 1992); Smith, Smith *Organic Synthesis, Second Edition* (McGraw-Hill Science/Engineering/Math, 2001); Bruggink A, *Synthesis of [beta]-lactam Antibiotics: Chemistry, Biocatalysis & Process Integration* (Springer, 2001.)

Compounds of this invention, for example those with phenylacetyl-NH— groups as the R—NH— groups in formulas herein, can be used as intermediates in the synthesis of beta-lactam compounds having various aminoacyl groups at this ring position. For example, modification of the R aminoacyl groups at the 7 position (or equivalent position) on the core ring system) can be accomplished by those of ordinary skill in the art using art-recognized techniques, starting materials and reagents which are available commercially or by application of art-known synthetic methods. Removal of the phenylacetyl group can be accomplished, for example, by deamidation through one of several methods including the use of $PCl_5$, penicillin amidase, cephalosporin C amidase or penicillin acylase to give the free amine at the 7 position (or equivalent position). The amino group can then be modified by reacting a functionalized carboxylic acid in the presence of penicillin amidase under acidic conditions or by activating the functionalized carboxylic acid with an activating agent such as cyclohexylcarbodiimide.

Mechanisms of Beta-Lactamase Inhibition

With out wishing to be bound by any particular mechanism of action of the compound herein, the following mechanistic discussion is provided to present the current view of the inventors with respect to the inhibition of beta-lactamases by compounds of this invention. It is believed that highly reactive electrophilic or nucleophilic sites (e.g., chemical moieties or groups) are generated in compounds of this invention upon opening of the βlactam ring, particularly by one or more beta-lactamases. The species generated on lactam ring opening are generated from certain latent reactive moieties or groups which are conjugated to the lactam ring in the compounds of this invention. These sites are believed capable of covalently binding to a beta-lactamase enzyme nucleophile or electrophile, respectively.

Schemes 1 and 2 illustrate examples of the generation of reactive nucleophiles which will react with enzyme groups such as serine, tyrosine, histidine, thiol, amines or combinations thereof. Covalent binding of the compounds of the invention is believed to inhibit the enzyme.

Schemes 3 and 4 illustrate examples of the generation of highly reactive nucleophilic moieties upon opening of the lactam ring. These compounds will work particularly well against the serine beta-lactamases enzymes. Because of their nonselectivity and high reactivity, they also target the met-allo-beta-lactamases which do not proceed through a stabile acylated enzyme intermediate. These are potent nucleophiles that can react with the abundant electrophilic centers in proteins; e.g., the carbonyls of the amide (peptide) bonds.

Scheme 5 illustrates inhibitor compounds of this invention which are multifunctional suicide inhibitors wherein multiple sites become activated on cleavage of the beta-lactam ring and thereby become available to alkylate the beta-lactamase enzyme.

Scheme 1

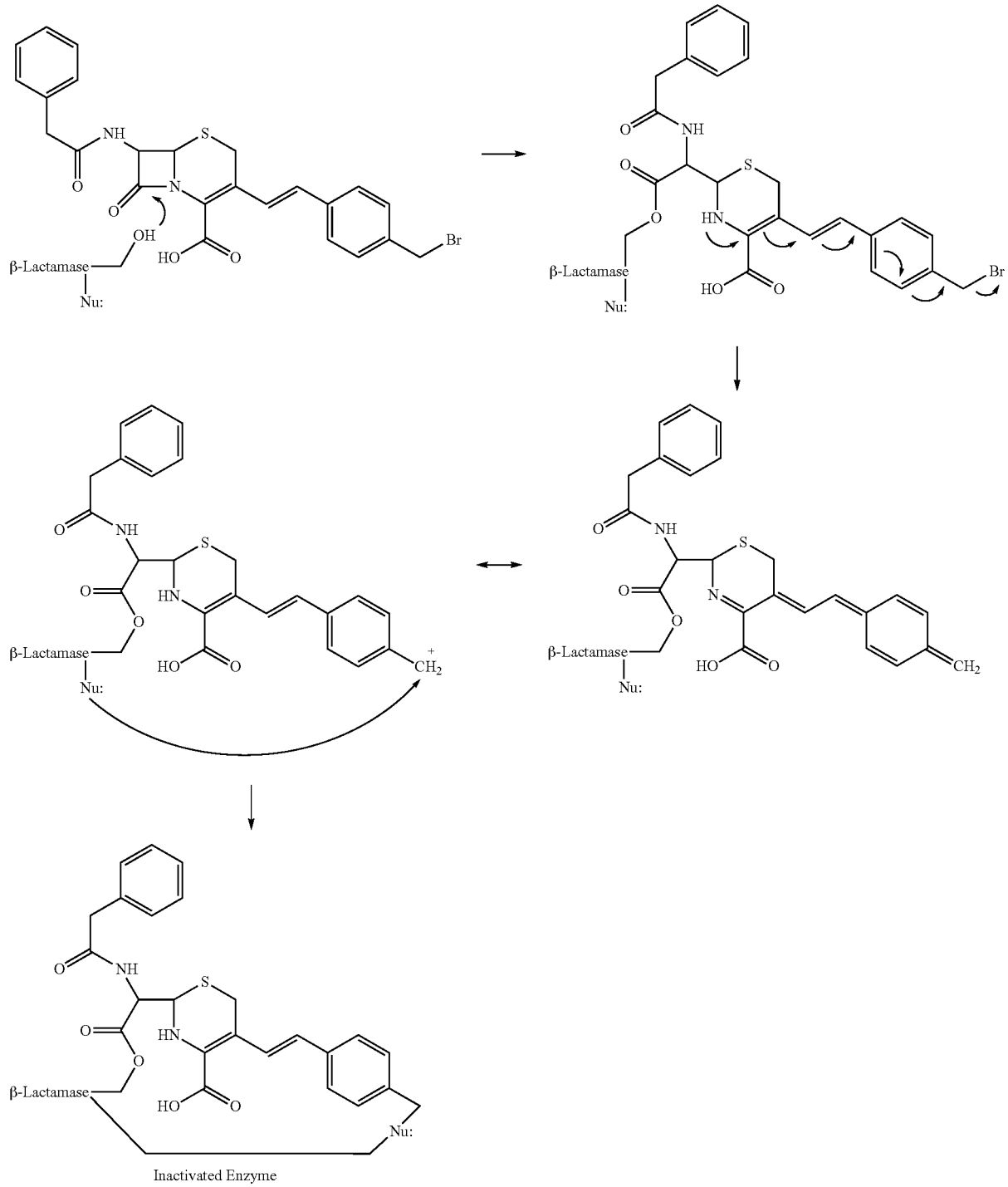

Scheme 2
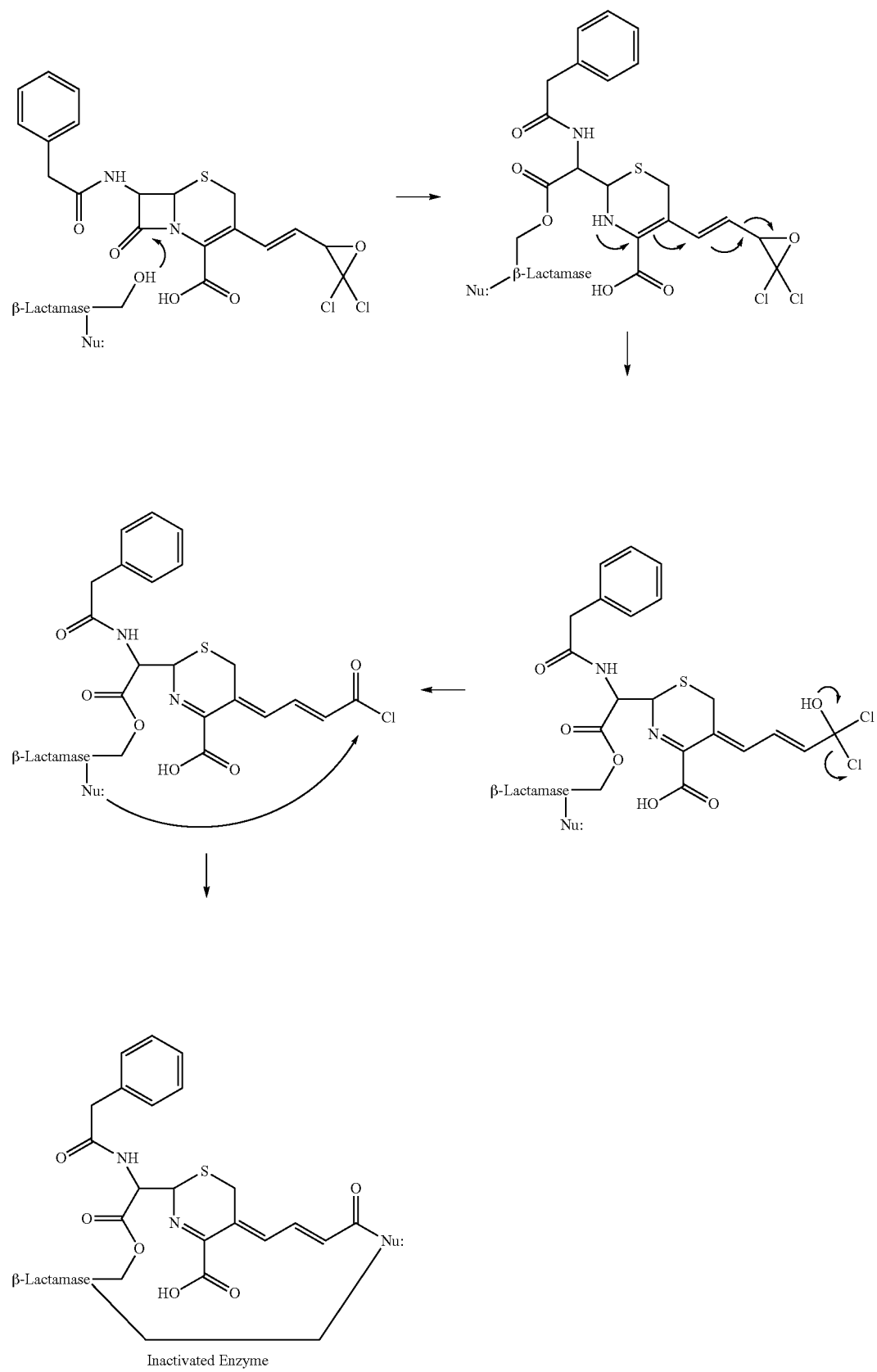
Inactivated Enzyme

Scheme 3
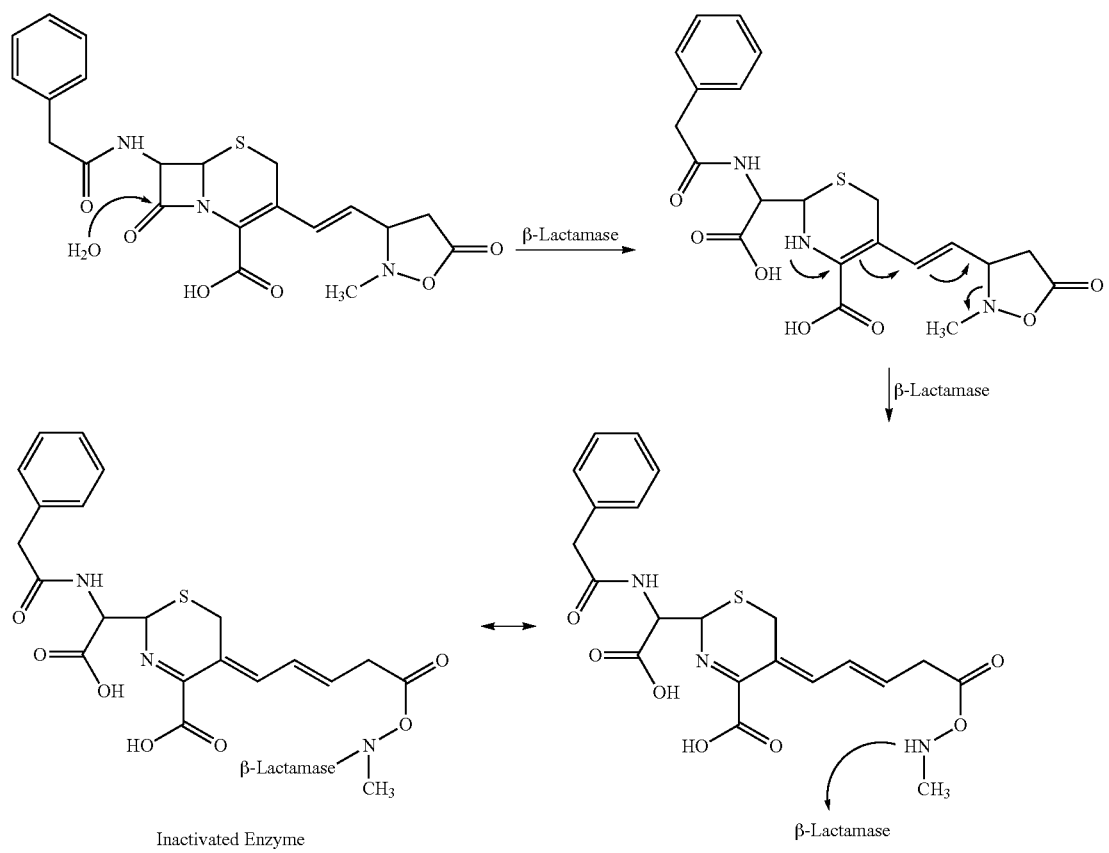
Scheme 4
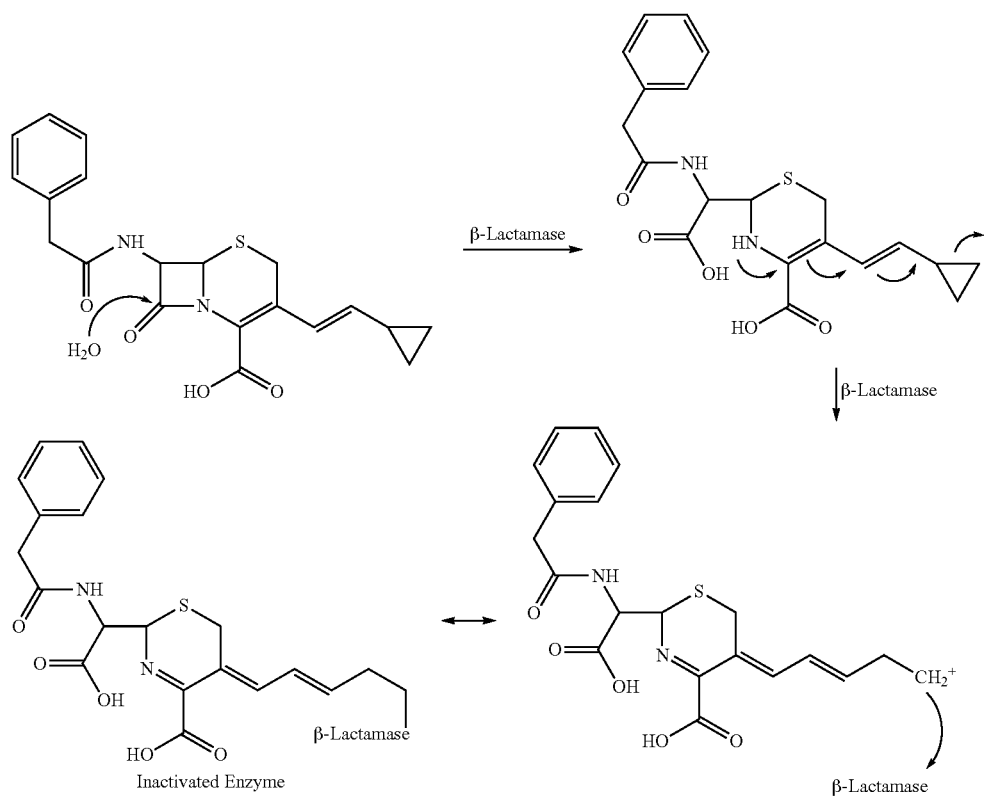

Scheme 5

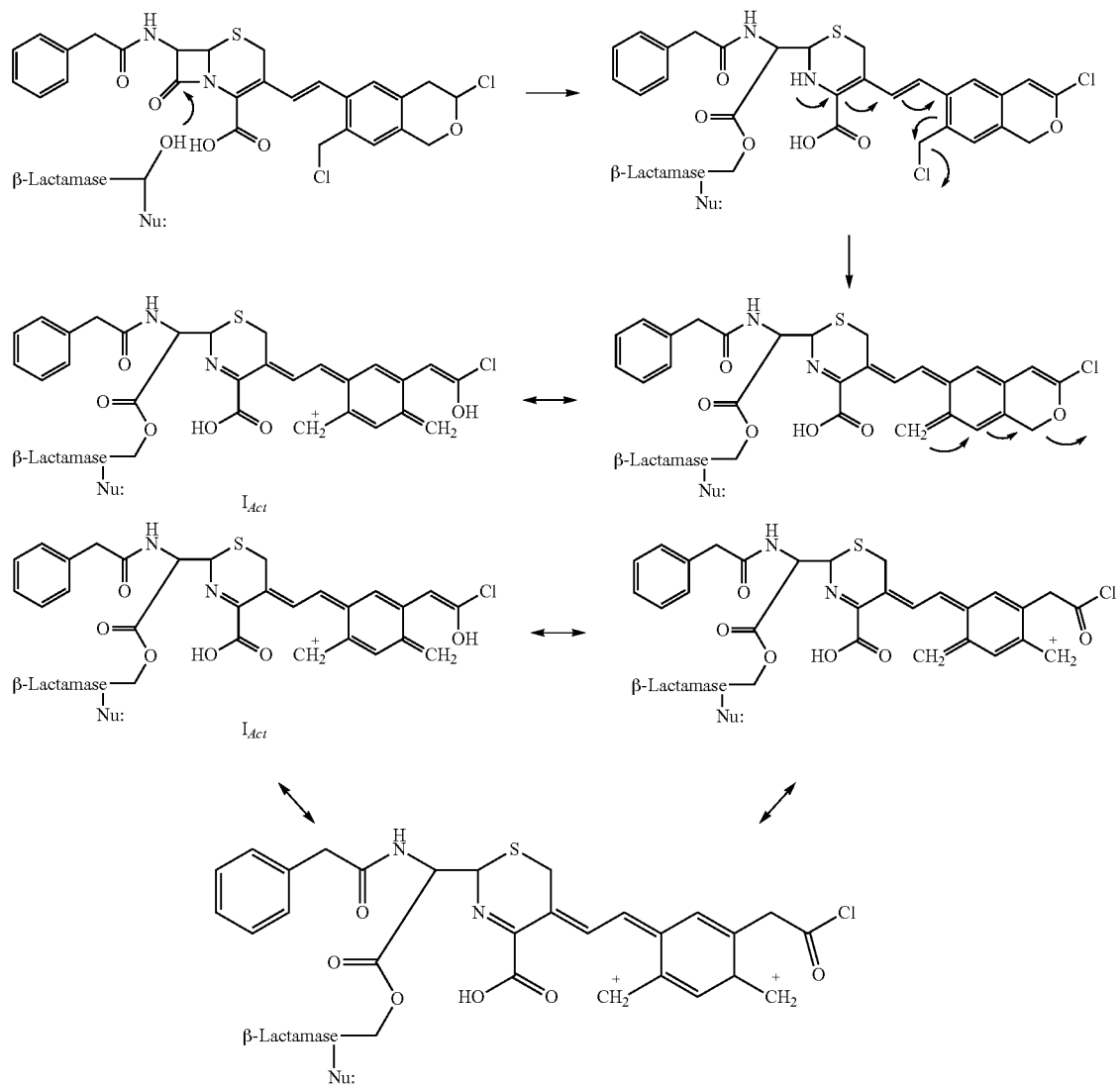

One of ordinary skill in the art will appreciate on review of Schemes 1-5 above, that alternative latent reactive moieties and groups can be introduced onto the vinyl group substituent on the various beta-lactam ring systems illustrated therein which will generate electrophilic or nucleophilic sites on cleavage of the beta-lactam ring by a beta-lactamase.

The compounds of this invention are typically administered to a patient in the form of a pharmaceutical composition. Accordingly, this invention provides pharmaceutical compositions comprising a pharmaceutically-acceptable carrier or excipient and a therapeutically effective amount of a compound of formula I-V or a pharmaceutically acceptable salt thereof.

Any conventional carrier or excipient may be used in the pharmaceutical compositions of this invention. The choice of a particular carrier or excipient, or combinations of carriers or excipients, will depend on the mode of administration being used to treat a particular patient or type of bacterial infection. The preparation of a suitable pharmaceutical composition for a particular mode of administration, such as oral, topical, inhaled, or parenteral administration, is well within the knowledge of those of ordinary skill in the pharmaceutical arts. Additionally, the ingredients for such compositions are commercially-available. For example, conventional formulations and formulations techniques are described in *Remington's Pharmaceutical Sciences*, 17.sup.th Ed. (Mace Publishing Co., 1985) and Banker, Rhodes (Eds) *Modern Pharmaceutics* 4th Edition (Marcel Dekker, Inc, 2002).

The pharmaceutical compositions of this invention will typically contain a therapeutically effective amount of a compound of formulas I-V or a pharmaceutically-acceptable salt thereof. The pharmaceutical compositions of this invention can contain a combined therapeutically effective amount of two or more compounds of formulas I-V or pharmaceutically-acceptable salts thereof. The pharmaceutical compositions of this invention can contain a combined therapeutically effective amount of one or more compounds of formulas I-V or pharmaceutically-acceptable salts thereof, in combination with one or more known beta-lactam antibiotics. Typically, such pharmaceutical compositions will contain from about 0.01 to about 99.99%, from about 0.1 to about 99.9%, from about 1% to 99%, form about 5% to about 95%, from about 10% to about 10% or from about 10% to about 50% of the active agent(s) of this invention. One of ordinary skill in the art knows or can readily determine therapeutically effective amounts of known beta-lactam antibiotics. Compounds of this invention can exhibit antibiotic activity and/or beta-lactamase inhibition. The amount or combined therapeutically effective amount of a compound of this invention for antibiotic effect may be different from that for beta-lactamase inhibition. One or ordinary skill in the art can determine therapeutically effective amounts of the compounds of this invention employing art-known techniques without undue experimentation. In pharmaceutical compositions in which a beta-lactamase inhibitor of this invention is combined with a known beta-lactamase antibiotic or a beta-lactamase antibiotic of this invention, the therapeutically effective amount typically employed will be that for achieving beta-lactamase inhibition.

Pharmaceutical compositions of this invention include those suitable for parenteral administration, particularly intravenous administration. Such pharmaceutical compositions typically comprise a sterile, physiologically-acceptable aqueous solution containing a therapeutically effective amount or combined amount of a compound of formulas I-V or pharmaceutically-acceptable salts thereof. Physiologically-acceptable aqueous carrier solutions suitable for intravenous administration of active agents are well-known in the art. Such aqueous solutions include among others, 5% dextrose, Ringer's solutions (lactated Ringer's injection, lactated Ringer's plus 5% dextrose injection, acylated Ringer's injection), Normosol-M, Isolyte E and the like. Optionally, such aqueous solutions may contain a co-solvent, for example, polyethylene glycol; a chelating agent, for example, ethylenediamine tetracetic acid; a solubilizing agent, for example, a cyclodextrin; an anti-oxidant, for example, sodium metabisulphite; and the like.

The aqueous pharmaceutical compositions of this invention can be lyophilized and subsequently reconstituted with a suitable carrier prior to administration. The carrier in this composition comprises, for example, sucrose, mannitol, dextrose, dextran, lactose or a combination thereof.

Pharmaceutical compositions of this invention include those for oral administration in which the active ingredient is combined with a solid carrier or excipient. Choice of carriers and excipients for oral dosage forms is within the knowledge of one of ordinary skill the art.

The pharmaceutical compositions of this invention can be packaged in a unit dosage form. This term refers to a physically discrete unit suitable for dosing a patient, i.e., each unit containing a predetermined quantity of active agent calculated to produce the desired therapeutic effect either alone or in combination with one or more additional units. Unit dosage forms include, among others, tablets, capsules, solutions, suspensions, elixirs, syrups, cream, lotions, ointments, sprays and aerosols. For example, such unit dosage forms may be packaged in sterile, bottles, vials, tubes, sprayers, aerosole dispensers, sealed ampoules and the like.

Compounds of the invention are useful as antibiotics. For example, the compounds of this invention are useful for treating or preventing bacterial infections and other bacteria-related medical conditions in mammals, including humans and animals (i.e., dogs, cats, horses, cows, pigs, etc.) which are caused by microorganisms susceptible to the compounds of this invention. This invention provides a method of treating a bacterial infection in a mammal, the method comprising administering to a mammal in need of treatment, a pharmaceutical composition comprising a pharmaceutically-acceptable carrier and a therapeutically effective amount or combined therapeutically effective amount of one or more compounds of formulas I-V, or pharmaceutically-acceptable salts thereof.

Compounds of the invention are useful as components of antibiotic compositions. For example, the compounds of this invention are useful in combination with known beta-lactam antibiotics for treating or preventing bacterial infections and other bacteria-related medical conditions in mammals, including humans and animals (i.e., dogs, cats, horses, cows, pigs, etc.) which are caused by microorganisms susceptible to the compounds of this invention. This invention provides a method of treating a bacterial infection in a mammal, the method comprising administering to a mammal in need of treatment, a pharmaceutical composition comprising a pharmaceutically-acceptable carrier and a combined therapeutically effective amount of a known beta-lactam antibiotic, including a beta-lactam antibiotic of this invention and one or more beta-lactamase inhibitors of formulas I-V, or pharmaceutically-acceptable salts thereof.

Compounds of this invention are useful for treating or preventing infections caused by Gram-positive bacteria and related microorganisms. For example, the compounds of this invention are effective for treating or preventing infections caused by certain *Enterococcus* spp.; *Staphylococcus* spp., including coagulase negative staphylococci (CNS); *Streptococcus* spp.; *Listeria* spp.; *Clostridium* ssp.; *Bacillus* spp.; and the like. Examples of bacterial species effectively treated with the compounds of this invention include, but are not limited to, methicillin-resistant *Staphylococcus aureus* (MRSA); methicillin-susceptible *Staphylococcus aureus* (MSSA); glycopeptide intermediate-susceptible *Staphylococcus aureus* (GISA); methicillin-resistant *Staphylococcus epidermitis* (MRSE); methicillin-sensitive *Staphylococcus epidermitis* (MSSE); vancomycin-sensitive *Enterococcus faecalis* (EFSVS); vancomycin-sensitive *Enterococcus faecium* (EFMVS); penicillin-resistant *Streptococcus pneumoniae* (PRSP); *Streptococcus pyogenes*; *Bacillus anthracis* and the like.

Compounds of this invention are useful for treating or preventing infections caused by Gram-negative bacteria and related microorganisms. For example, the compounds of this invention are effective for treating or preventing infections cause by certain *Escherichia* spp.; *Salmonella* spp.; *Neisseria* spp.; *Helicobacter* spp.; and the like. Examples of bacterial species effectively treated with the compounds of this invention include, but are not limited to *Escherichia coli* 0157:H7; *Salmonella enterica*; *Salmonella typhi*; *Shigella dysenteriae*; *Yersinia pestis*; *Pseudomonas aeruginosa*; *Vibrio cholerae*; *Bordetalla petussis*; *Haemophilus influenzae*; *Helicobacter pylori*; *Helicobacter felis*; *Campylobacter jejuni*; *Neisseria gonorrhoeae*; *Neisseria meningitides*; *Brucella abortus*; *Bacteroides fragilis*; and the like.

Compounds of this invention are also useful for treating or preventing infections caused by bacteria not traditionally categorized by Gram stain including but not limited to *Treponema pallidum*; *Borrelia burgdorferi*; *Rickettisas* spp.; and the like.

Exemplary types of infections or bacteria-related medical conditions which can be treated or prevented with the compounds of this invention include, but are not limited to, skin and skin structure infections, urinary tract infections, pneumonia, endocarditis, catheter-related blood stream infections, osteomyelitis, and the like. In treating such conditions, the patient may already be infected with the microorganism to be treated, be suspected of being infected with the microorganism or merely be susceptible to infection in which case the active agent is administered prophylactically.

The compounds of this invention are typically administered in a therapeutically effective amount by any acceptable route of administration. The compounds may be administered in a single daily dose or in multiple doses per day. The treatment regimen may require administration over extended periods of time, for example, for several days or for one to six weeks or longer. The amount of active agent administered per dose or the total amount administered will typically be determined by the patient's physician and will depend on such factors as the nature and severity of the infection, the age, weight and general health of the patient, the tolerance of the patient to the active agent, the microorganism(s) causing the infection, the route of administration and the like. Typical dosage ranges for beta-lactam antibiotics are 100 mg to several grams.

Additionally, the compounds of this invention are generally effective for inhibiting the growth of bacteria. In this embodiment, bacteria are contacted either in vitro or in vivo with a growth-inhibiting amount of a compound of formula I-V or pharmaceutically-acceptable salts thereof. Inhibition of bacterial growth is typically evidenced by a decrease or lack of reproduction by the bacteria and/or by lysis of the bacteria, i.e., by a decrease in colony-forming units in a given volume over a given period of time (i.e., per hour) compared to untreated bacteria. Compounds of this invention may be bacteriostatic or bacteriocidal. Typical concentrations of beta-lactam antibiotics effective for bacterial growth inhibition rang from tenths of micrograms to tens of micrograms per mL.

Additionally, the compounds of this invention are generally effective for inhibiting beta-lactamases. In this embodiment, the beta-lactamase is contacted in vitro or in vivo with an inhibiting amount of a compound of formula I-V or pharmaceutically-acceptable salts thereof. Typical effective concentrations of beta-lactam inhibitors for inhibiting beta-lactamases range from tenths of micrograms to tens of micrograms per mL.

The compounds of this invention can also inhibit cell wall biosynthesis in bacteria. In this embodiment, bacterial are contacted either in vitro or in vivo with a cell wall biosynthesis-inhibiting amount of a compound of formula I or pharmaceutically-acceptable salt thereof. Typical effective concentrations of beta-lactam inhibitors for inhibiting cell wall biosynthesis range from tenths of micrograms to tens of micrograms per mL.

This invention additionally relates to the use of one or more compounds of this invention in the manufacture of a medicament for treatment of microbial infection, particularly bacterial infections and particularly infection of bacterial which exhibit resistance to one or more beta-lactam antibiotics because of the presence of beta-lactamases. The medicament comprises therapeutically effective amounts or combined amounts of one or more compounds of this invention, particularly those compounds which exhibit microbial and/or bacterial inhibition. More specifically, the invention relates to the use of one or more compounds of the formulas herein in the manufacture of a medicament for treatment of such microbial and bacterial infections. In specific embodiments the medicament manufactured is in suitable dosage form for oral, optical, parenteral, or other form suitable form of administration as a tablet, capsule, solution, cream ointment, or other suitable dosage for. In specific embodiments, the medicament further comprises a pharmaceutically acceptable carrier, excipient, or diluent and particularly a carrier or diluent suitable for oral or parenteral administration.

This invention further relates to the use of one or more compounds of this invention as beta-lactamase inhibitors in the manufacture of a medicament for treatment of microbial infection, particularly bacterial infections and particularly infection of bacterial which exhibit resistance to one or more beta-lactam antibiotics because of the presence of beta-lactamases. In this embodiment, the medicament further comprises a therapeutically effective amount of a beta-lactam antibiotic. More specifically, the invention relates to the use of one or more compounds of the formulas herein in the manufacture of a medicament for treatment of such microbial and bacterial infections. In specific embodiments the medicament manufactured is in suitable dosage form for oral, optical, parenteral, or other form suitable form of administration as a tablet, capsule, solution, cream ointment, or other suitable dosage for. In specific embodiments, the medicament further comprises a pharmaceutically acceptable carrier, excipient, or diluent and particularly a carrier or diluent suitable for oral or parenteral administration.

In specific embodiments, the invention provides the use of one or more compounds of this invention in the manufacture of a medicament for treatment of microbial infection, particularly bacterial infections and particularly infection of bacterial which exhibit resistance to one or more beta-lactam antibiotics because of the presence of beta-lactamases. In specific embodiments the medicament manufactured is in an oral or parenteral dosage form such as tablet, capsule or solution. In specific embodiments, the medicament further comprises a pharmaceutically acceptable carrier or diluent and particularly a carrier or diluent suitable for oral or parenteral administration.

Without wishing to be bound by any particular theory, there can be discussion herein of beliefs or understandings of underlying principles and mechanisms of action relating to the invention. It is recognized that regardless of the ultimate correctness of any mechanistic explanation or hypothesis, an embodiment of the invention can nonetheless be operative and useful.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group members are intended to be individually included in the disclosure. A number of specific groups of variable definitions have been described herein. It is intended that all combinations and subcombinations of the specific groups of variable definitions are individually included in this disclosure. Specific names of compounds are intended to be exemplary, as it is known that one of ordinary skill in the art can name the same compounds differently.

Compounds described herein may exist in one or more isomeric forms, e.g., structural or optical isomers. When a compound is described herein such that a particular isomer, enantiomer or diastereomer of the compound is not specified, for example, in a formula or in a chemical name, that description is intended to include each isomers and enantiomer (e.g., cis/trans isomers, R/S enantiomers) of the compound described individual or in any combination.

Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Isotopic variants, including those carrying radioisotopes, may also be useful in biological research, diagnostic assays and in therapeutics. Methods for making such isotopic variants are known in the art.

Molecules disclosed herein may contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

One of ordinary skill in the art will appreciate that synthetic methods, starting materials, reagents, beta-lactamases, beta-lactam antibiotics, commercially available beta-lactam antibiotics, enzyme assays, beta-lactamase activity assays, pharmaceutical formulations and dosage forms, other than those specifically exemplified can be employed in the practice of the invention without resort to undue experimentation. All art-known functional equivalents, of any such assay methods, starting materials, synthetic methods, starting materials, reagents, beta-lactamases, beta-lactam antibiotics, commercially available beta-lactam antibiotics, enzyme assays, beta-lactamase activity assays, pharmaceutical formulations and dosage forms are intended to be included in this invention.

Whenever a range is given in the specification, for example, a range of numbers of elements in a chemical group or moiety (e.g., a range of numbers of carbons (e.g., C1-C3)), a range of any integer, a range of any number of substituents, a temperature range, a time range, or a composition range, all intermediate ranges and subranges, as well as all individual values included in the ranges given are intended to be included in the disclosure. It will be understood that any subranges or individual value or values in a range or subrange that are included in the description can be excluded from the claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the broad term "comprising", particularly in a description of components of a composition or in a description of elements of a device, is intended to encompass and describe the terms "consisting essentially of" or "consisting of". The invention illustratively described herein suitably may be practiced in the absence of any element or elements, limitation or limitations which is not specifically disclosed herein.

Although the description herein contains many specifics, these should not be construed as limiting the scope of the invention, but as merely providing illustrations of some of the embodiments of the invention. All references cited herein, other than patent documents to which priority is claimed, are hereby incorporated by reference to the extent that there is no inconsistency with the disclosure of this specification. Some references provided herein are incorporated by reference herein to provide details concerning additional starting materials, additional methods of synthesis, additional methods of analysis and additional uses of the invention.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by examples, preferred embodiments and optional features, modification and variation of the concepts herein disclosed may be resorted to by those skilled in the art, and that such modifications and variations are considered to be within the scope of this invention as defined by the appended claims.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when compounds are claimed, it should be understood that compounds known and available in the art prior to Applicant's invention, including compounds for which an enabling disclosure is provided in the references cited herein, can be excluded included in the compound claims herein. Some references provided herein are incorporated by reference to provide details concerning synthetic methods, starting materials, reagents, known-beta-lactam antibiotics, pharmaceutical formulations and components of such formulations, methods of administration of such pharmaceutical composition, purification methods, and methods of analysis; as well as additional uses of the invention.

THE EXAMPLES

Example 1

Assay (I) for Beta-Lactamase Activity

A chromogenic cephalosporin, Cefesone, is synthesized and isolated as described by Sutton et al. and used to monitor p-lactamase activity. A typical assay monitors the hydrolysis of Cefesone via the formation of a species which absorbs at 486 nm (molar absorptivity constant 16,000). Absorption is monitored as a function of time in 0.1 M, pH 7.0 sodium phosphate, 0.2 mM Cefesone and 4 volume percent DMSO cosolvent at 30° C. using a Beckman DU-40 spectrophotometer having a circulating water bath attached to the cuvette holder. The assay is initiated by addition and mixing of an appropriate amount of beta-lactamase.

Assay (II) for Beta-Lactamase Activity

Another method of monitoring for beta-lactamase activity involved dissolving enough Cefesone in ethyl acetate to make a solution of 3 micrograms per microliter. Ten microliters of this solution is then applied to a 6 mm diffusion disc. To monitor activity, the disc is dampened with water and a small aliquot of a beta-lactamase containing solution is applied to the disc and a color change from light yellow to deep magenta is monitored visually. Typically time is recorded to first detectable visible color change.

Example 2

The following example is directed to synthesis of compounds of one preferred subset of compounds of formula I, those having a cephem nucleus and an M group having a cyclopropane ring (XX):

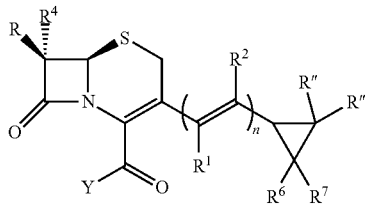

XX where variables are as defined in various formulas above. The method applies more specifically to compounds of formula XX where R is R'—NH—, an amine, where in formula XX, R' most generally R is a proton or a pharmacologically acceptable functional group or salt, each $R^1$, $R^2$, each R", $R^6$ and $R^7$, independently, are selected from hydrogens, halogens or organic functional groups, including alkyl functionalized carbonyl, esters, carbamates, and other electron withdrawing groups. The method more specifically applies to compounds of formula XX where each R", $R^6$, and $R^7$ are selected from the group consisting of hydrogen, halogens, carbonyl groups, alkylcarbonyl groups, alkoxycarbonyl groups, aromatic carbonyl groups, carboxylate esters, aromatic carboxylic esters, primary, secondary, and tertiary aliphatic and aromatic amines. In this subset of compounds the N of the beta-lactam ring system is conjugated to the electron withdrawing cyclopropyl group in M via a pi-electron system. This conjugation facilitates electronic rearrangement to open the cyclopropyl ring after the lactam ring is opened (for example by a beta-lactamase enzyme).

One method of synthesizing cephem compounds (formula XX) is by reacting a compound of formula XXI or formula XXII or reactive derivatives thereof with a compound of formula XXIII or a reactive derivative thereof:

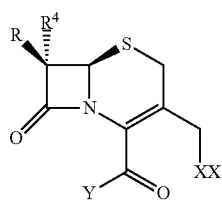

XXI

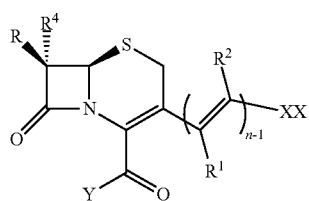

XXII where XX, in formulas XXI and XXII, represents any halogen such as chloride, bromide or iodide and the 4-carboxylate group (—CO—Y) can be protected if needed to carry out the reaction;

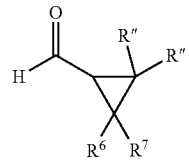

XXIII

Compounds of formula XX can also be synthesized by reacting a compound of formula XXIV or a reactive derivative thereof with a compound of formula XXV:

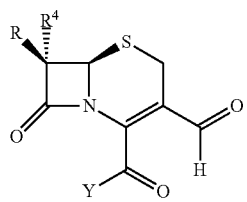

XXIV

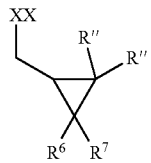

XXV

After reaction, removal of any protecting groups of the 4-carboxylate can be accomplished by conventional art-known methods. When R is an amine or functionalizing the 7-amino position with groups such as acyl groups to form aminoacyl groups can be accomplished according to conventional methods by those of ordinary skill in the art. When R is an aminoacyl group, methods for converting one aminoacyl group into another aminoacyl group can also be accomplished according to conventional methods by those of ordinary skill in the art. Isomerization of the unsaturated bonds formed in synthesis of compounds of structure XX can be performed by conventional methods by those skilled of ordinary skill in the art. The method illustrated can be readily adapted by one of ordinary skill in the art to obtain $R^1$ and $R^2$ groups other than hydrogen.

Representative Synthetic Example

Synthesis of 3-Vinylcyclopropane-7-(2-Phenylacetamido)-3-Cephem-4-carboxylic Acid In 20 ml of methylene chloride and 10 ml of THF was dissolved 1 gram (2 mmol) of 4-methoxybenzyl 3-chloromethyl-7-(2-phenylacetamido)-3-cephem-4-carboxylate, 800 mg (3 mmol) triphenylphosphine, and 1.4 grams (20 mmol) cyclopropane carboxaldehyde. To this solution was added 400 mg (2.5 mmol) KI and 5 ml 10% sodium bicarbonate. The mixture was stirred vigorously in the dark overnight according to the method of U.S. Pat. No. 6,417,351 (Jul. 9, 2002) Kameyama. The aqueous phase was separated and discarded. The organic phase was washed thrice with water, dried with magnesium sulfate, and concentrated. The product was purified by flash vacuum chromatography by elution first with methylene chloride which eluted the excess triphenylphosphine and cyclopropane carboxaldehyde followed by chloroform which eluted the desired product. The fractions with similar product Rf on silica gel TLC with toluene to ethyl acetate (5:1 v:v) were pooled and solvent evaporated to obtain the 4-carboxyl protected compound (I) where stereochemistry of the cephem ring is not specifically shown, but is that shown in formula XX:

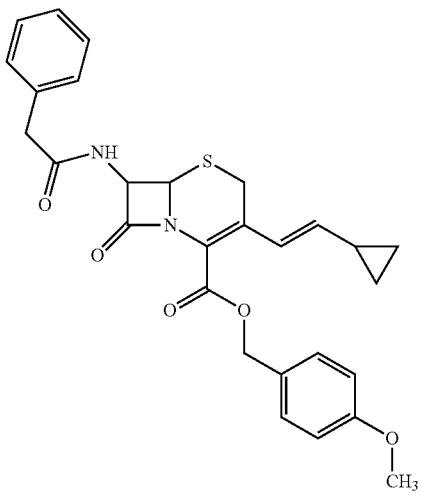

1

The protected product 1 was dissolved in methylene chloride and treated with TFA and anisole according to the method of Lee et al. (2005) J. Organ. Chem. 70(1): 367-369. The solvents were rapidly evaporated and 3-vinylcyclopropane-7-(2-phenylacetamido)-3-Cephem-4-carboxylic acid 2 (again stereochemistry of the cephem ring is not shown, but is that of formula XX) was isolated by trituration with petroleum either as a yellow solid.

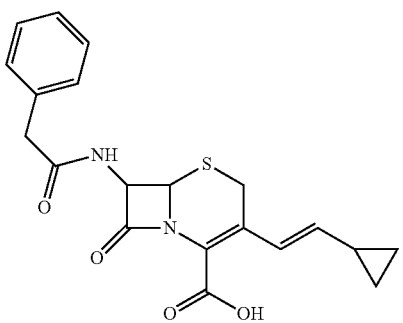

2

The methods illustrated can be employed to modify beta-lactam molecules, conferring on them the property of forming one or more reactive intermediate in the beta-lactam compound upon opening of the lactam ring system. The reactive intermediate is then able to react with and irreversibly inhibit one or more beta-lactamases.

Example 3

Product Inhibition of Beta-Lactamase

The beta-lactamase assay using enzyme from *Enterobacter cloacae* (Sigma-Aldrich, St. Louis, Mo.) was carried out as in Example 1 (assay I) above with compound 2. After the initial rate was determined the reaction was allowed to continue for two hours. Theoretical maximal absorbance at 486 nm is approximately 1.6 while the observed final absorbance was consistently 0.26. This result is consistent with product inhibition as illustrated by the following equation:

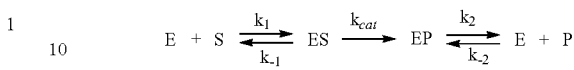

where E is enzyme, S is substrate, P is product, ES is the enzyme-substrate complex, EP is the enzyme product complex, and $k_1$, $k_{-1}$, $k_2$, and $k_{-2}$ are rate constants and kcat is the catalytic rate constant. In the case of product inhibition $k_{-2}$ is large with respect to $k_2$, so as enzyme product accumulates, more enzyme is tied up in the enzyme-product complex and is unavailable for catalysis.

Example 4

Time Dependent Inhibition of beta-Lactamase by 3-Vinylcyclopropane-7-(2-Phenylacetamido)-3-Cephem-4-carboxylic Acid (2)

The initial control rate without inhibitor is determined by adding to one microL of 0.1 M sodium phosphate buffer (pH 7.0), 10 microL DMSO and 5 microL 0.1 unit/mL beta-lactamase from *Enterobacter cloacae* at 30° C. The reaction is initiated by addition of 20 microL 0.1 mM Cefesone in DMSO and the initial rate is determined. Inhibition reactions are determined by substituting the DMSO with 0.1 mM 3-vinylcyclopropane-7-(2-phenylacetamido)-3-Cephem-4-carboxylic acid 2 in DMSO and incubating for increasing periods of time before initiating the reaction by addition of Cefesone. The inactivation profile at 200 microM 3vinyl-cyclopropane-7-(2-Phenylacetamido)-3-Cephem-4-carboxylic acid is illustrated in FIG. 1. Dialysis of 10 mL 0.1 units/mL beta-lactamase with and without 500 microM inhibitor against 1 L of 0.1 M sodium phosphate buffer (pH 7.0) with one exchange revealed no return of activity.

Example 5

The following example is directed to synthesis of compounds of one preferred subset of compounds of formula I, those having a cephem nucleus and an M group having a phenyl ring carrying one or more appropriately positioned leaving groups (XXV1). The phenyl ring and its leaving groups are conjugated through a pi-electron system to the N of the beta-lactam ring.

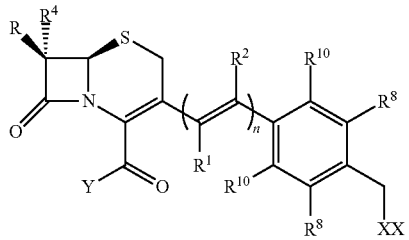

XXVI

In formula XXVI, most generally the variables are defined as for formula I above. More specifically, $R^{10}$ and $R^8$ are exemplified by hydrogen, halogens, thiol, groups carrying carbonyls, alkylcarbonyl groups, alkoxycarbonyl groups, aromatic groups, substituted aromatic groups, carboxylate esters, aromatic carboxylic esters, primary, secondary, ant-tertiary aliphatic and aromatic amines, wherein XX represents a good leaving group conjugated to the lactam nitrogen. More specifically, R, Y and $R^1$ and $R^2$ are as defined for formula XX in Example 2. Again the —CO—Y group may be a protected carbonyl, if desirable. In specific embodiments, $R^{10}$ and $R^8$ are hydrogens or methyl groups. In specific methods the leaving group is a halogen, particularly I, Br or Cl, pyridinium, or thiol group, and most specifically Br.

Methods of synthesis are analogous to those in Example 2. One method of synthesizing cephem compounds (XXVI) is by reacting a compound of the formula XXI or Xxii (above, Example 2) or reactive derivatives thereof with a compound of formula XXVII or a reactive derivative thereof:

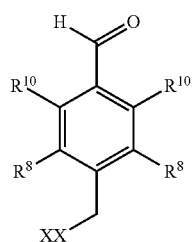

XXVII

Compounds of formula XXVI can also be synthesized by reacting a compound of formula XXIV (Example 2) or a reactive derivative thereof with a compound of formula XXVIII:

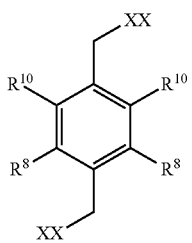

XXVIII where the each XX variable is the same leaving group, e.g, Br. One of ordinary skill in the art can adapt the method, if desired, so that the leaving group of the product XXVI is different from that of the intermediate XXVIII.

After reaction, removal of any protecting groups of the 4-carboxylate can be accomplished by conventional art-known methods. When R is an amine or functionalizing the 7-amino position with groups such as acyl groups to form aminoacyl groups can be accomplished according to conventional methods by those of ordinary skill in the art. When R is an aminoacyl group methods for converting one aminoacyl group into another aminoacyl group can also be accomplished according to conventional methods by those of ordinary skill in the art. Isomerization of the unsaturated bonds formed in synthesis of compounds of structure XXVI can be performed by conventional methods by those skilled of ordinary skill in the art. The method illustrated can be readily adapted by one of ordinary skill in the art to obtain $R^1$ and $R^2$ groups other than hydrogen.

Representative Synthetic Example

Synthesis of 3-(1-Bromomethyl-4-Vinylbenzene)-7-(2-Phenylacetamido)-3-Cephem-4-carboxylic Acid (1) In 75 mL acetone was dissolved 972 mg 4-methoxybenzyl 3-chloromethyl-7-(2-phenylacetamido)-3-cephem-4-carboxylate (2 mmol) and 410 mg KI. Immediately a fine cloudy precipitate formed. The mixture was stirred for 3 hours, the acetone evaporated and the mixture taken up in 35 mL methylene chloride. The mixture was filtered, solids discarded and mother liquor retained with the product, 4-methoxybenzyl 3-iodomethyl-7-(2-phenylacetamido)-3-cephem-4-carboxylate.

(2) Triphenylphosphine (0.81 grams) was dissolved in the mother liquor and the solution stirred in the dark overnight to form 4-methoxybenzyl 3-phosphonium bromide methyl-7-(2-phenylacetamido)-3-cephem-4-carboxylate salt.

(3) The solution was diluted with an additional 50 mL methylene chloride then vigorously stirred with 50 mL saturated sodium bicarbonate. To this slurry was slowly added 1.22 grams 4-bromomethyl benzaldehyde dissolved in 31 mL methylene chloride over a period of 0.5-1 hour. The reaction was then stirred overnight.

(4) The organic layer was separated and retained, washed twice with 1.0 N NaCl and dried with magnesium sulfate. The solvent was then evaporated to give an oil residue which was then dissolved in a minimum of methylene chloride. The product was purified by flash vacuum chromatography by elution first with methylene chloride which eluted the excess triphenylphosphine and cyclopropane carboxaldehyde followed by chloroform which eluted the desired product. The fractions with similar product Rf on silica gel TLC with toluene to ethyl acetate (5:1 v:v) were pooled and solvent evaporated to obtain the protected product 3.

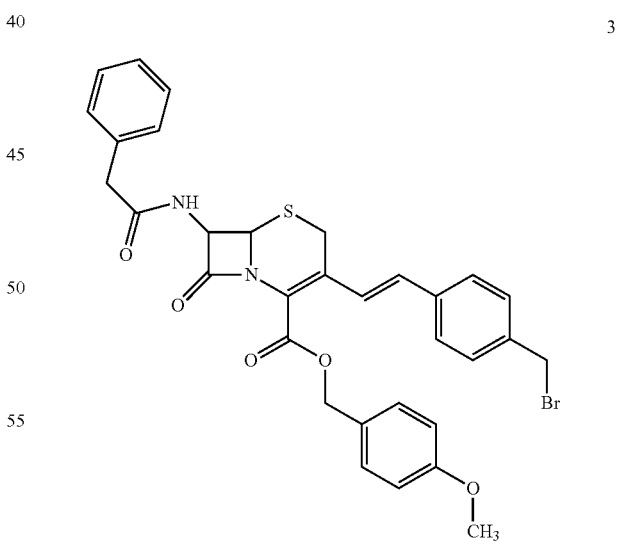

3

The product (3) was dissolved in methylene chloride and treated with TFA and anisole according to the method of Lee et al. The solvents were rapidly evaporated and 3-(1-bromomethyl-4-vinylbenzene)-7-(2-phenylacetamido)-3-Cephem-4-carboxylic acid (4) was isolated by trituration with petroleum ether as a yellow solid.

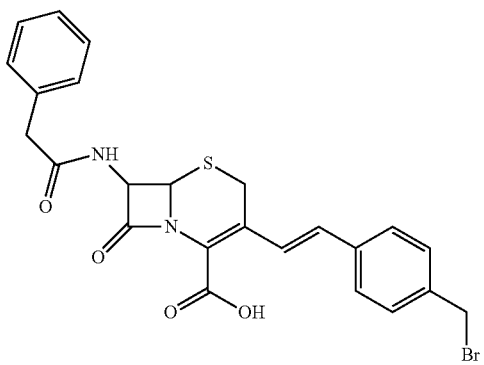

4

Example 6

The assay for beta-lactamase inhibition of compound 4 is carried out as in Example 3 again using the enzyme for *Enterobacter cloacae*.

Figure 2:
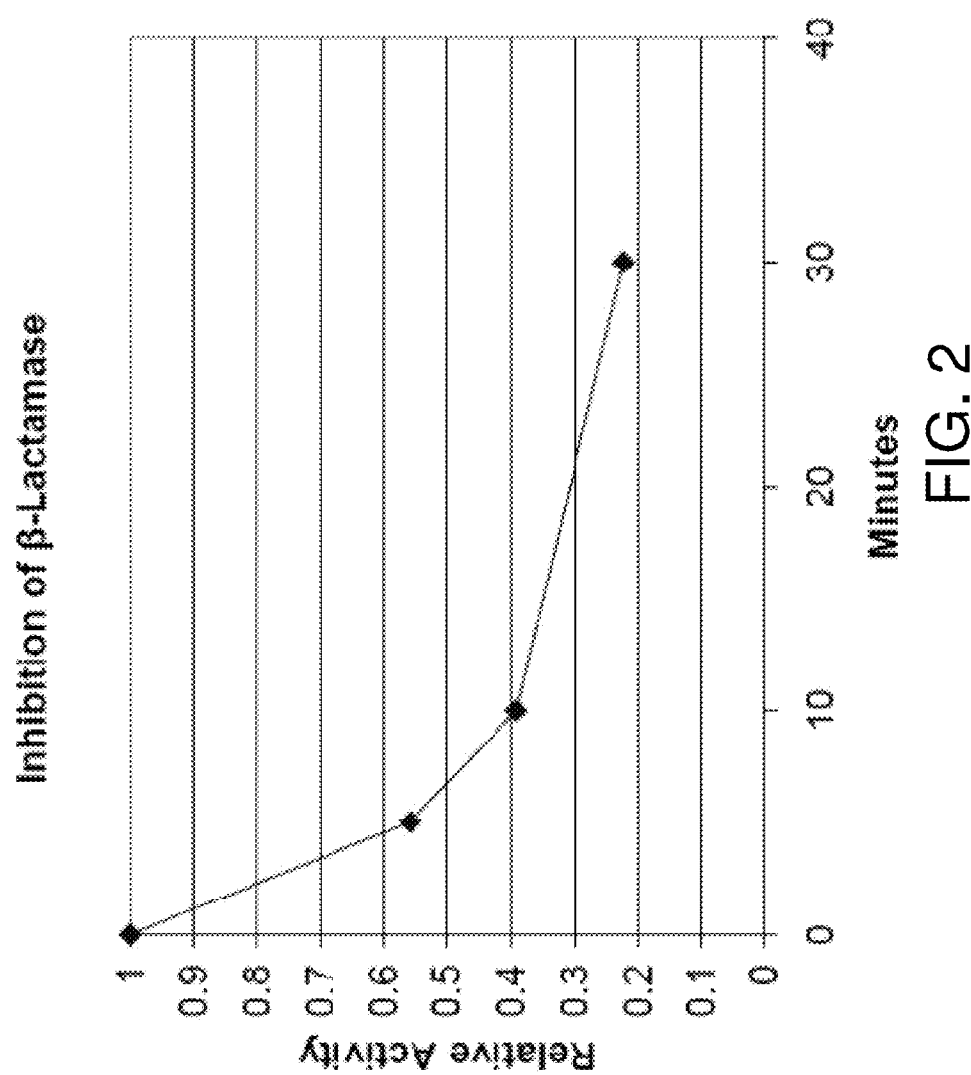
FIG. 2 is a graph of time dependent Inhibition of a beta-lactamase by 3-(1-bromomethyl-4-vinylbenzene)-7-(2-phenylacetamido)-3-Cephem-4-carboxylic acid (XI).

Time dependent inhibition of beta-lactamase by compound XI is carried out as in Example 4. The inactivation profile at 100 microM 3-(I-bromomethyl-4-vinylbenzene)-7-(2-phenylacetamido)-3-cephem-4-carboxylic acid is illustrated in FIG. 2.

Dialysis of 10 mL 0.1 units/mL beta-lactamase with and without 500 microM inhibitor against 1 L of 0.1 M sodium phosphate buffer (pH 7.0) with one exchange revealed no return of activity.

Example 7

Synthesis of 4-diphenylmethyl-3-[-2-(3,3-dicholoroxiran-2-yl)vinyl]-7-(2-phenylacetamido)-3-cephem-4-carboxylate In 20 mL of methylene chloride and 10 mL of THF is dissolved 1 gram (2 mmol) of 4-diphenylmethyl-3-chloromethyl-7-(2-phenylacetamido)-3-cephem-4-carboxylate, 800 mg (3 mmol) triphenylphosphine, and 2.8 grams (20 mmol) 3,3-dichlorooxirane-2-carboxaldehyde. To this solution is added 400 mg (2.5 mmol) KI and 5 mL 10% sodium bicarbonate. The mixture is stirred vigorously in the dark overnight according to the method of Kameyama supra. The aqueous phase is separated and discarded. The organic phase is washed thrice with water, dried with magnesium sulfate, and concentrated. The product is purified by flash vacuum chromatography by elution first with methylene chloride which elutes the excess triphenylphosphine and aldehyde followed by chloroform which elutes the desired product. The fractions with similar product Rf on silica gel TLC with toluene to ethyl acetate (5:1 v/v) are pooled and solvent evaporated to provide protected product 5.

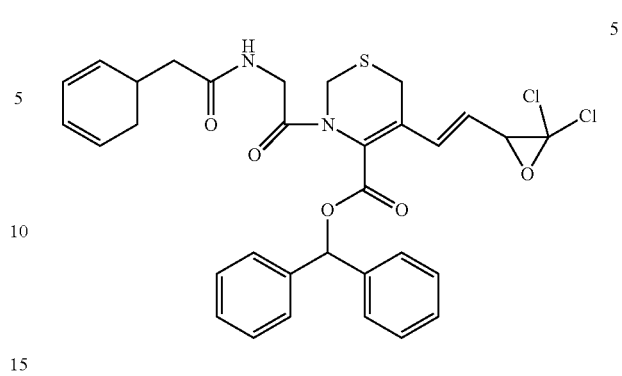

5

Synthesis of 3-[-2-(3,3-dicholoroxiran-2-yl)vinyl]-7-(2-phenylacetamido)-3-cephem-4-carboxylic Acid The product (5) is dissolved in methylene chloride and treated with TFA and anisole according to the method of Lee et al. The solvents are rapidly evaporated and the title compound (6) is isolated by trituration with petroleum ether.

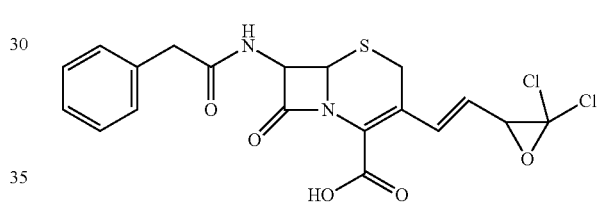

6

Example 8

Synthesis of 4-diphenylmethyl-3-[-2-(2-methyl-5-oxoisoxazolidin-3-yl)vinyl]-7-(2-phenylacetamido)-3-cephem-4-carboxylate In 20 mL of methylene chloride and 10 mL of THF is dissolved 1 gram (2 mmol) of 4-diphenylmethyl-3-chloromethyl-7-(2-phenylacetamido)-3-cephem-4-carboxylate, 800 mg (3 mmol) triphenylphosphine, and 2.8 grams (20 mmol) 3,3-dichlorooxirane-2-carboxaldehyde. To this solution is added 400 mg (2.5 mmol) KI and 5 mL 10% sodium bicarbonate. The mixture is stirred vigorously in the dark overnight according to the method of Kameyama supra. The aqueous phase is separated and discarded. The organic phase is washed thrice with water, dried with magnesium sulfate, and concentrated. The product is purified by flash vacuum chromatography by elution first with methylene chloride which elutes the excess triphenylphosphine and aldehyde followed by chloroform which elutes the title compound 7. The fractions with similar product Rf on silica gel TLC with 5:1 toluene to ethyl acetate is pooled and solvent evaporated to obtain the protected product 7:

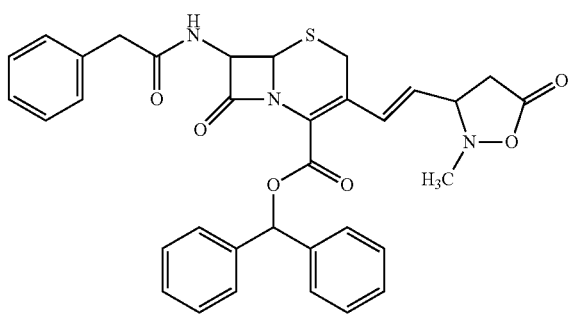

Synthesis of 3-[-2-(2-methyl-5-oxoisoxazolidin-3-yl)vinyl]-7-(2-phenylacetamido)-3-cephem-4-carboxylate The protected product 7 is dissolved in methylene chloride and treated with TFA and anisole according to the method of Lee et al. supra The solvents were rapidly evaporated and the title compound 8 is isolated by trituration with petroleum ether.

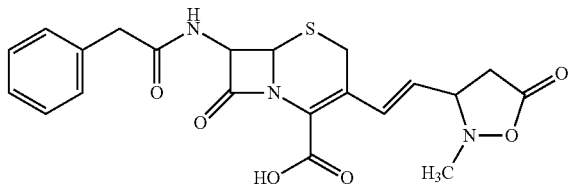

Example 9

Synthesis of 4-methoxybenzyl-3-(1-Pyridinium Methyl-4-Vinylbenzene)-7-(2-Phenylacetamido)-3-Cephem-4-carboxylate In 20 mL methylene chloride is dissolved 1.21 grams (2 mmol) 4-methoxybenzyl-3-(1-bromomethyl-4-vinylbenzene)-7-(2-phenylacetamido)-3-cephem-4-carboxylate and 160 milligrams pyridine and stirred overnight in darkened container. The methylene chloride is removed under vacuum and the title compound 9 is collected.

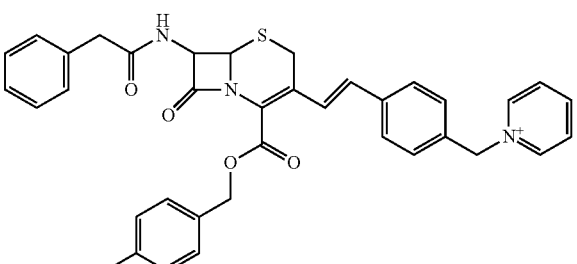

(e.g., as a bromide salt)

Synthesis of 3-(1-Pyridinium Methyl-4-Vinylbenzene)-7-(2-Phenylacetamido)-3-Cephem-4-carboxylic Acid (as a Bromide Salt)

The protected product 9 is dissolved in methylene chloride and treated with TFA and anisole according to the method of Lee et al. supra. The solvents are rapidly evaporated and the title compound 10 is isolated by trituration with petroleum ether.

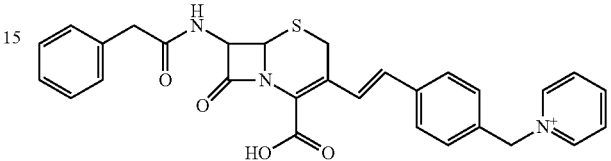

The foregoing examples are illustrative of the methods and compounds of the invention and are not intended to limit the scope of the invention.

The invention claimed is:

1. A compound of formula I:

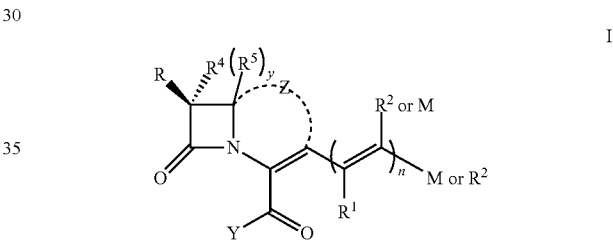

or a pharmacologically acceptable salt thereof, wherein:

R is an acylamino group or an optionally substituted benzyl-NH— group;

$R^1$ and $R^2$ are independently selected from hydrogen, halogen, a C1-C6 alkyl group, a C1-C6 alkoxy group and a —S—C1-C6-alkyl group;

n is an integer ranging from 1-5;

—Z— is present or absent and represents —O—$(CH_2)x$-, —C—$(CH_2)x$-, —NR'—$(CH_2)x$-, —SO—$(CH_2)x$-, or —$SO_2$—$(CH_2)x$-, where x is 0 or 1 and R' is hydrogen or a C1-C6 alkyl group, when —Z— is present, y is 1 and when it is absent, y is 2;

Y is O—$C^+$ or $OR^3$, where $R^3$ is hydrogen, or an optionally substituted alkyl or aryl group and $C^+$ is a pharmacologically acceptable cation;

$R^4$ is hydrogen, a C1-C6 alkyl group, or OR', where R' is hydrogen or a C1-C6 alkyl group;

$R^5$ is hydrogen, or a C1-C6 alkyl group; and

M represents a chemical species which is in the cis or trans position with respect to $R^1$, and which is selected from the group consisting of P, B, BZ, D, E, and F as follows:

P

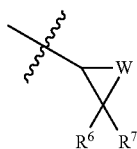

where:
W is O or C(R") and each R" for W groups is independently selected from the group consisting of hydrogen, halogen, a C1-C6 alkyl group, a C2-C6 alkenyl group, a C2-C6 alkynyl group, a C7-C19 aralkyl group, a 3-7-member-ring cyclic hydrocarbon group, a 3-7-member-ring heterocyclic group, a C6-C10 aromatic group and a 6-10-member-ring heterocyclic aromatic group, wherein each of said groups is optionally substituted; and $R^6$ and $R^7$ are independently selected from hydrogen, halogen, a C1-C6 alkyl group, a C2-C6 alkenyl group, a C2-C6 alkynyl group, a C7-C19 aralkyl group, a 3-7-member-ring cyclic hydrocarbon group, a 3-7-member-ring heterocyclic group, a C6-C10 aromatic group, a 6-10-member-ring heterocyclic aromatic group, a —COR" group, a —COOR" group, and a —CON(R")$_2$ group, wherein each R" for $R_6$ and $R_7$ groups is independently selected from the group consisting of hydrogen, a C1-C6 alkyl group, a C2-C6 alkenyl group, a C2-C6 alkynyl group, a C7-C19 aralkyl group, a 3-7-member-ring cyclic hydrocarbon group, a 3-7-member-ring heterocyclic group, a C6-C10 aromatic group and a 6-10-member-ring heterocyclic aromatic group, wherein each of said groups is optionally substituted;

B

BZ

D

E and

F where:
$Z^2$ is O, $NR^{11}$ or S, where $R^{11}$ is selected from the group consisting of hydrogen, a C1-C6 alkyl group, a C2-C6 alkenyl group, and a C2-C6 alkynyl group, wherein each group is optionally substituted;

each $R^8$ is independently selected from hydrogen, halogen, a C1-C6 alkyl group, a C2-C6 alkenyl group, a C2-C6 alkynyl group, a C7-C19 aralkyl group, a 3-7-member-ring cyclic hydrocarbon group, a 3-7-member-ring heterocyclic group, a C6-C10 aromatic group, 6-10-member-ring heterocyclic aromatic group, a C1-C6 alkoxy group, a —S—C1-C6-alkyl group, a —CO—R' croup, a —CO$_2$R' croup, a —CO—N(R')$_2$ group;

a —N(R')$_2$ group, a —NR'—CO—R' group, and a —NR'CO$_2$—R' group, wherein each R' for $R^8$ groups is independently selected from hydrogen, a C1-C6 alkyl group, a C2-C6 alkenyl group, a C2-C6 alkynyl group, a C7-C19 aralkyl group, a 3-7-member-ring cyclic hydrocarbon group, a 3-7-member-ring heterocyclic group, a C6-C10 aromatic group and a 6-10-member-ring heterocyclic aromatic group, wherein each of said groups is optionally substituted; and each $R^9$ is independently selected from hydrogen, a C1-C6 alkyl group, a C2-C6 alkenyl group, a C2-C6 alkynyl group, a C7-C19 aralkyl group, a 3-7-member-ring cyclic hydrocarbon group, a 3-7-member-ring heterocyclic group, a C6-C10 aromatic group and a 6-10-member-ring heterocyclic aromatic group, wherein each of said groups is optionally substituted;

each $R^{10}$ is independently selected from the group consisting of a —CH$_2$—X group, hydrogen, halogen, a C1-C6 alkyl group, a C2-C6 alkenyl group, a C2-C6 alkynyl group, a C7-C19 aralkyl group, a 3-7-member-ring cyclic hydrocarbon group, a 3-7-member-ring heterocyclic group, a C6-C10 aromatic group, 6-10-member-ring heterocyclic aromatic group, a C1-C6 alkoxy group, a —S—C1-C6-alkyl group, a —CO—R' group, a —CO$_2$R' group, a —CO—N(R')$_2$ group; a —N(R')$_2$ group, a —NR'—CO—R' group, and a —NR'—CO$_2$—R' group, wherein each R' for $R^{10}$ groups is independently selected from hydrogen, a C1-C6 alkyl group, a C2-C6 alkenyl group, a C2-C6 alkynyl group, a C7-C19 aralkyl group, a 3-7-member-ring cyclic hydrocarbon group, a 3-7-member-ring heterocyclic group, a C6-C10 aromatic group, and a 6-10-member-ring heterocyclic aromatic group, wherein each of said groups is optionally substituted;

$R^{12}$ is selected from the group consisting of X, hydrogen, a C1-C6 alkyl group, a C2-C6 alkenyl group, a C2-C6 alkynyl group, a C7-C19 aralkyl group, a 3-7-member-ring cyclic hydrocarbon group, a 3-7-member-ring heterocyclic group, a C6-C10 aromatic group, a 6-10-member-ring heterocyclic aromatic group, a C1-C6 alkoxy group, a —S—C1-C6-alkyl group, a —CO—R' group, a —CO$_2$R' group, a —CO—N(R')$_2$ group; a —N(R')$_2$ group, a —NR'—CO—R' group, and a —NR'—CO$_2$—R' group, wherein each R' for $R^{12}$ groups is independently selected from hydrogen, a C1-C6 alkyl group, a C2-C6 alkenyl group, a C2-C6 alkynyl group, a C7-C19 aralkyl group, a 3-7-member-ring cyclic hydrocarbon group, a 3-7-member-ring heterocyclic group, a C6-C10 aromatic group, and a 6-10-member-ring heterocyclic aromatic group, wherein each of said groups is optionally substituted;

$R^{13}$ and $R^{14}$ are independently selected from the group consisting of X, hydrogen, a C1-C6 alkyl group, a C2-C6 alkenyl group, a C2-C6 alkynyl group, a C7-C19 aralkyl group, a 3-7-member-ring cyclic hydrocarbon group, a 3-7-member-ring heterocyclic group, a C6-C10 aromatic group, a 6-10-member-ring heterocyclic aromatic group, a C1-C6 alkoxy group, a —S—C1-C6-alkyl group, a —CO—R' group, a —CO$_2$R' group, a —CO—N(R')$_2$ group; a —N(R')$_2$ group, a —NR'—CO—R' group, and a —NR'—CO$_2$—R' group, wherein each R' for $R^{13}$ and $R^{14}$ groups is independently selected from hydrogen, a C1-C6 alkyl group, a C2-C6 alkenyl group, a C2-C6 alkynyl group, a C7-C19 aralkyl group, a 3-7-member-ring cyclic hydrocarbon group, a 3-7-member-ring heterocyclic group, a C6-C10 aromatic group, and a 6-10-member-ring heterocyclic aromatic group, wherein each of said groups is optionally substituted;

wherein optional substitution includes substitution with one or more groups selected from a C1-C3 alkyl group, a C6-C12 aryl group, a C1-C3 haloalkyl group, I, Cl, Br, F, —CN, —OH, a C1-C3 alkoxy group, a —O-aryl group, a —O-benzyl group, a -phenoxy group, —SH, a —S—C1-C3-alkyl group, a —S-phenyl group, a —S-benzyl group, —NH$_2$, and a —N(R$^{16}$)$_2$ group, where each R$^{16}$ is a C1-C3 alkyl group, a benzyl group or a phenyl group;

wherein X is a leaving group;

wherein the compound contains one $R^2$ and one M group; and wherein in structures B and Bz at least one $R^{10}$ is a —CH$_2$—X group, in structure E at least one $R^{10}$ is a —CH$_2$—X group, or $R^{12}$ is X and in structure F one of $R^{13}$ or $R^{14}$ is X.

2. The compound or pharmaceutically acceptable salt of claim claim 1 of formula:

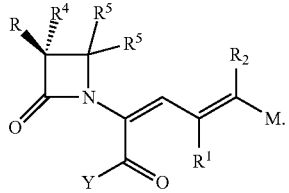

3. The compound or pharmaceutically acceptable salt of claim 2, wherein:

$R^1$ and $R^2$ are independently selected from hydrogen, halogen, a C1-C6 alkyl group, a C1-C6 alkoxy group and a —S—C1-C6-alkyl group;

$R^4$ is hydrogen;

Y is —O$^-$ C$^+$ or —OR$^3$, where $R^3$ is hydrogen, an alkyl group or an aryl group, each of which groups is optionally substituted, and C$^+$ is a pharmacologically acceptable cation; and M is selected from:

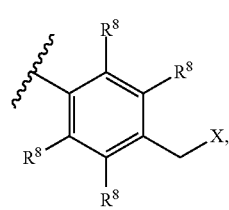

B1

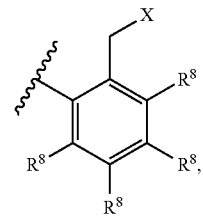

B2

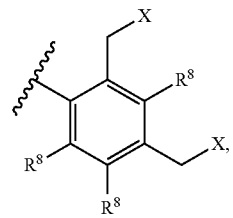

B3

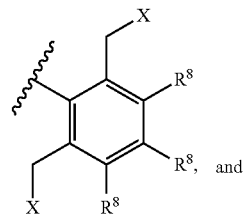

B4

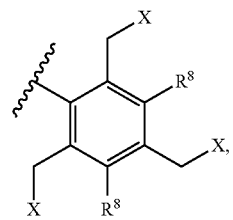

B5 where:

each $R^8$ is independently selected from hydrogen, halogen, a C1-C6 alkyl group, a C2-C6 alkenyl group, a C2-C6 alkynyl group, a C7-C19 aralkyl group, a 3-7-member ring cyclic hydrocarbon group, a 3-7-member-ring heterocyclic group, a C6-C10 aromatic group, and a 6-10-member-ring heterocyclic aromatic group, wherein each of said groups is optionally substituted, and X is a leaving group selected from halogen, a pyridinium group, a —SC(O)R' group, a —OCOR' group, —SH, a —SR' group, a phenoxy group, a pentafluorophenoxy group, and a tosyl group, where R' for the listed groups is selected from optionally substituted alkyl and aryl groups.

4. The compound or pharmaceutically acceptable salt thereof of claim 3, where both $R^5$ are hydrogens.

5. The compound or pharmacologically acceptable salt thereof of claim 4, wherein X is a halogen or a pyridinium group and each $R^8$ is independently hydrogen, an optionally substituted C1-C6 alkyl group or an optionally substituted C6-C12 aryl group.

6. The compound or pharmaceutically acceptable salt thereof of claim 4, wherein X is a halogen and each $R^8$ is independently hydrogen, an optionally substituted C1-C6 alkyl group or an optionally substituted C6-C12 aryl group.

7. The compound or pharmacologically acceptable salt thereof of claim 4, wherein M is:

49

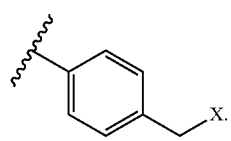
5

8. The compound or pharmacologically acceptable salt thereof of claim 7, wherein X is a leaving group selected from halogen, a pyridinium group, a phenoxy group, a pentafluorophenoxy group, and a tosyl group.

9. The compound or pharmacologically acceptable salt thereof of claim 7, wherein X is halogen or a pyridinium group.

10. The compound or pharmacologically acceptable salt thereof of claim 7, wherein X is Cl or Br.

11. The compound or pharmacologically acceptable salt thereof of claim 2, wherein the acyl group of the acylamino group of R is selected from:

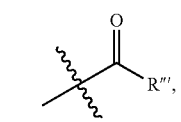
A1

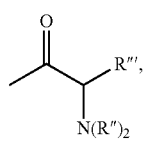
A2

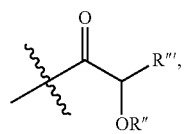
A3

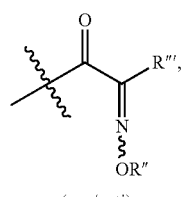
A4
(syn/anti)

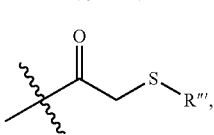
A5

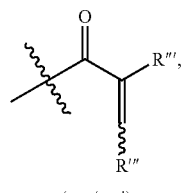
A6
(syn/anti)

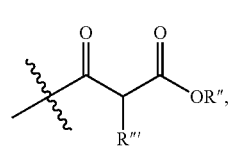
A7

50
-continued

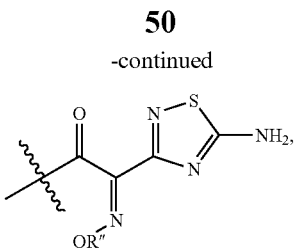
A9

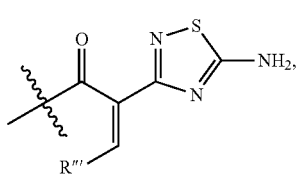
A10

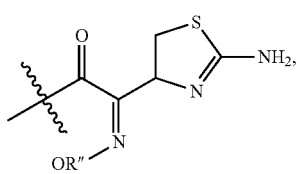
A11

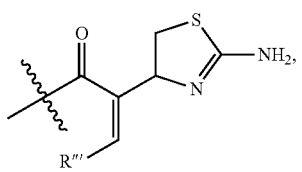
A12

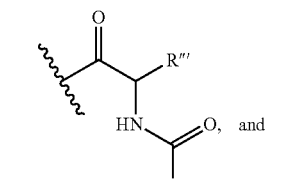
A13

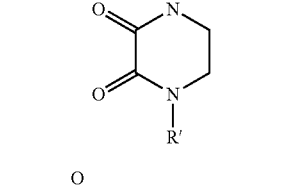
A14

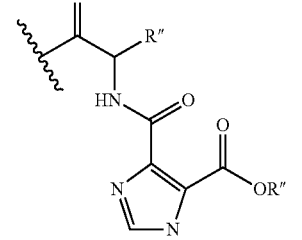

where in A1-A14, R' is selected from hydrogen, a C1-C6 alkyl, and a C6-C12 aryl;

R" is selected from hydrogen, a C1-C6 alkyl group, a C2-C6 alkenyl group, a C2-C6 alkynyl group, a C7-C19 aralkyl group, a 3-7-member-ring cyclic hydrocarbon group, a 3-7-member-ring heterocyclic group, a C6-C10 aromatic group and a 6-10-member-ring heterocyclic aromatic group; and R''' is selected from hydrogen, C1-C6 alkyl group, a C2-C6 alkenyl group, a C2-C6 alkynyl group, a C7-C19 aralkyl group, a 3-7-member-ring cyclic hydrocarbon group, a 3-7-member-ring heterocyclic group, a C6-C10 aromatic group, a 6-10-member-ring heterocyclic aromatic group, a —CO—R$^{15}$, a —CO$_2$R$^{15}$, a —CO—N(R$^{15}$)$_2$, a —N(R$^{15}$)$_2$, a —NR$^{15}$—CO—R$^{15}$, and a —NR$^{15}$CO$_2$—R$^{15}$, wherein each R$^{15}$ is independently selected from hydrogen, a C1-C6 alkyl group, a C2-C6 alkenyl group, a C2-C6 alkynyl group, a C7-C19 aralkyl group, a 3-7-member-ring cyclic hydrocarbon group, a 3-7-member-ring heterocyclic group, a C6-C10 aromatic group, and a 6-10-member-ring heterocyclic aromatic group, wherein each of said groups is optionally substituted.

12. The compound or pharmacologically acceptable salt thereof of claim 11, wherein R$^4$ and each R$^5$ are hydrogens and M is:

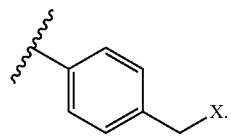

13. The compound or pharmacologically acceptable salt thereof of claim 12, wherein X is a leaving group selected from halogen, a pyridinium group, a phenoxy group, a pentafluorophenoxy group, and a tosyl group.

14. The compound or pharmacologically acceptable salt thereof of claim 12, wherein X is halogen or a pyridinium group.

15. A pharmaceutical composition comprising a therapeutically effective amount of one or more compounds of claim 1.

16. A pharmaceutical composition comprising a therapeutically effective amount of one or more compounds of claim 2.

17. A method of treatment of bacterial infections, which comprises the step of administering a therapeutically effective amount of one or more compounds of claim 1 to an individual in need of treatment.

18. A method of inhibiting the growth of a microorganism which comprises the step of contacting the microorganism with an effective amount of one or more compounds claim 1.

19. A method for inhibiting a beta-lactamase which comprises the step of contacting the beta-lactamase with an effective amount of a compound of claim 1.

20. The compound or pharmacologically acceptable salt thereof of claim 2, wherein:

R$^1$, R$^2$, R$^4$ and each R$^5$ is hydrogen;

n is 1; and

M is selected from:

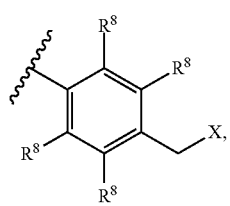

B1

-continued

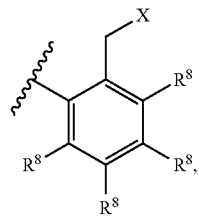

B2

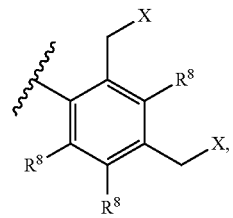

B3

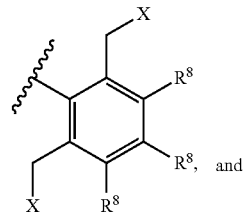

B4

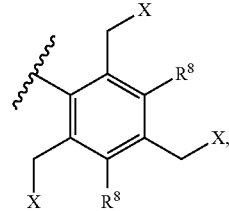

B5 where:
each R$^8$ is hydrogen, and X is a leaving group selected from halogen, a pyridinium group, a —SC(O)R' group, a —OCOR' group, —SH, a —SR' group, a phenoxy group, a pentafluorophenoxy group, and a tosyl group, where R' for the listed groups is selected from optionally substituted alkyl and aryl groups.

21. The compound or pharmacologically acceptable salt thereof of claim 20, wherein:
X is a leaving group selected from halogen, a pyridinium group, a pentafluorophenoxy group, and a tosyl group.

22. The compound or pharmacologically acceptable salt thereof of claim 20 of formula:

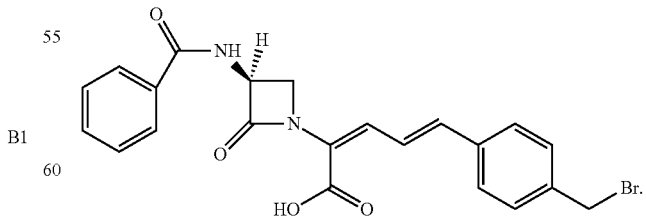

23. A method of treatment of bacterial infections, which comprises the step of administering a therapeutically effective amount of one or more compounds of claim 3 to an individual in need of treatment.

24. A method of inhibiting the growth of a microorganism which comprises the step of contacting the microorganism with an effective amount of one or more compounds claim 3.

25. A method for inhibiting a beta-lactamase which comprises the step of contacting the beta-lactamase with an effective amount of a compound of claim 3.

\* \* \* \* \*

UNITED STATES PATENT AND TRADEMARK OFFICE
CERTIFICATE OF CORRECTION

PATENT NO. : 9,453,032 B2  
APPLICATION NO. : 14/491806  
DATED : September 27, 2016  
INVENTOR(S) : Larry Sutton et al.

Page 1 of 1

It is certified that error appears in the above-identified patent and that said Letters Patent is hereby corrected as shown below:

At Column 46 Line 22 (Claim 1), replace "croup" with --group-- (two instances).

At Column 47 Line 38 (Claim 2), replace "claim claim 1 of formula" with --claim 1 of formula--.

Signed and Sealed this
Twenty-eighth Day of August, 2018

Andrei Iancu
*Director of the United States Patent and Trademark Office*